(12) United States Patent
Northrop et al.

(10) Patent No.: US 6,410,245 B1
(45) Date of Patent: Jun. 25, 2002

(54) COMPOSITIONS AND METHODS FOR DETECTING LIGAND-DEPENDENT NUCLEAR RECEPTOR AND COACTIVATOR INTERACTIONS

(75) Inventors: Jeffrey P. Northrop, Redwood City; Charles P. Hart; Peter J. Schatz, both of Mountain View, all of CA (US)

(73) Assignee: Affymax, Inc., Palo Alto, CA (US)

( * ) Notice: Subject to any disclaimer, the term of this patent is extended or adjusted under 35 U.S.C. 154(b) by 0 days.

(21) Appl. No.: 09/053,611

(22) Filed: Apr. 1, 1998

(51) Int. Cl.$^7$ .................. G01N 33/53; G01N 33/566
(52) U.S. Cl. .................. 435/7.1; 435/7.2; 435/69.1; 436/518; 424/141.1; 536/23.1; 536/23.5
(58) Field of Search .................. 436/518; 424/141.1; 536/23.5, 23.1; 435/7.1, 7.2, 69.1

(56) References Cited

U.S. PATENT DOCUMENTS

| | | | |
|---|---|---|---|
| 5,470,952 A | | 11/1995 | Stahl et al. |
| 5,679,582 A | * | 10/1997 | Bowie et al. ............... 436/518 |
| 5,688,504 A | * | 11/1997 | Morgan, Jr. ............... 424/141 |
| 5,688,938 A | * | 11/1997 | Brown et al. ............. 536/23.5 |
| 5,906,920 A | * | 5/1999 | Evans et al. ................ 435/7.1 |

FOREIGN PATENT DOCUMENTS

WO      95/26400    * 10/1995

OTHER PUBLICATIONS

Heery et al., A signature Motif in Transcriptional . . . , Nature, vol. 387, pp. 733–736, Jun. 12, 1997.*
Gietz et al., Identification of Proteins that Interact . . . , Molecular and Cellular Biology, vol. 172, pp. 67–79, Jul. 1, 1997.*

Bartel et al., Analyzing Protein–Protein Interaction . . . , Methods in Enzymology, vol.254, pp. 241–263, 1995.*

Heery et al. (1997), "A signature motif in transcriptional co–activators mediates binding to nuclear receptors," Nature 387:733–736.

Le Douarin et al. (1995), "A new version of the two–hybrid assay for detection of protein–protein interactions," Nucl. Acids Res. 23(5):876–878.

Traish et al. (1995), "Binding of site–directed monoclonal antibodies to an epitope located in the A/B region (amino acids 140–154) of human estrogen receptor–induced conformational changes in an epitope in the DNA–binding domain," Steroids 61(9):549–556.

* cited by examiner

*Primary Examiner*—Bennett Celsa
(74) *Attorney, Agent, or Firm*—Townsend and Townsend and Crew LLP

(57) ABSTRACT

The invention provides methods for identifying agents that are ligands for nuclear receptors. The methods include conducting multiplexed assays utilizing positive hybrid systems, reverse hybrid systems, direct interaction assays and other assays to screen for ligands having activity with a receptor of interest. The methods can be performed in various multiplexing formats to produce a profile that can be used to categorize a test ligand relative to known agonists and antagonists.

17 Claims, 20 Drawing Sheets

MAMMALIAN TWO-HYBRID ASSAY
RECEPTOR
COACTIVATOR
SRC-1 689-697
SRC-1 45-53
CBP 68-76
COREPRESSOR
REPORTER
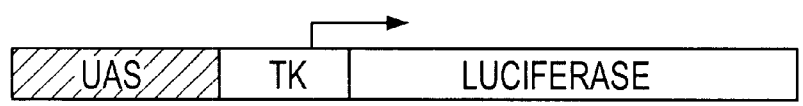
FIG.6

ERβ lacI SEQUENCES

| CLONE # | SEQUENCE | ELISA SIGNAL (+E2) |
|---|---|---|
| | -2 -1 +1 +2 +3 +4 +5 | |
| lib. | x x x x x x x L x x L L x x x x x x x | |
| 16 | V L E [K] [R] P I L [R] E L L [R] G P | 1.11 |
| 17 | G [R] N G S V I L [R] [R] L L N S G G S Y S N | 0.95 |
| 9 | H S M N H S I L T [R] L L T S S V G M Q | 0.93 |
| 21 | C A [R] D M S [K] L Q [R] L L [R] G L P A | 0.88 |
| 8 | V G F S L [R] [R] L E T L L [R] E G R I N D | 0.60 |
| 10 | T [R] [R] E A S [K] L C S L L I G G | 0.54 |
| 5 | E T A [K] E S L L W [R] L L E [R] G S T E [R] | 0.52 |
| 14 | Q L A S S A [K] L V S L L Q S | 0.44 |
| 13 | [R] G N [R] L S [R] L S Q L L G N S E I G G | 0.30 |
| 3 | S S H [K] G S [K] L [K] S L L Q F G P | 0.29 |
| 12 | G G A [R] D T M L E A L L [K] C S G A G I N | 0.26 |
| lib. RANDOM 15-mer | | |
| 42 | P I L [R] [R] L L T T [R] Q M [R] L I | 0.40 |
| 31 | G P Q T G S L L W [K] M L A E [R] | 0.30 |
| 41 | G S T M S I L L A E L L [R] [R] G | 0.25 |
| 38 | S V G I L [R] [R] L L E N [K] E E | 0.22 |
| 44 | [R] T Q S L L [R] T L L T A D L T | 0.22 |

FIG.16

ERβ MBP SEQUENCES

```
(LXXLL)       X  X  X  X  X  X  X  L  X  X  L  L  X  X  X  X  X  X   ELISA
                                                                      SIGNAL
                                                                      (+E2)
                       -2 -1 +1 +2 +3 +4 +5
M-8           L  C  S  T [R] P  L  L  Y [R] L  L  L  S [K] G  C  N  W   0.67
M-13         [K] D  S [R] A  H  L  L [R] D  V  L  V  M  K  S  E         0.25
M-1           G  S [K] H  G  V  L  L [R] H  L  L [R] V  E  E  S [R]     0.22
M-57          L [R] G [R] Q  P  M  L [R] G  L  L  C [R] S  E  V [R][R]  0.19
M-70          E  S  C  H [R] S  L  L  H  S  L  L  L  T                  0.18

RANDOM 15-MER

|  | | LIGAND | | | | |
|---|---|---|---|---|---|---|
| | | ESTRADIOL | LIGAND X | LIGAND Y | LIGAND Z | TAMOXIPHEN |
| POSITIVE HYBRID ASSAY | LBD-1 + CA-1 | + | + | - | - | - |
| | LBD-1 + CA-2 | - | - | - | ++ | ++ |
| | LBD-1 + CR-1 | + | - | + | - | - |
| | LBD-2 + CA-1 | - | - | - | +/- | + |
| | LBD-2 + CA-2 | EC50= 0.5nM | EC50= 0.9nM | EC50= 30nM | EC50= 15nM | EC50= 200nM |
| | LBD-2 + CR-1 | - | - | + | + | - |
| INTERACTION ASSAY | LBD-1 + CA-1 | +++ | ++ | + | + | + |

← ESTROGEN-LIKE  TAMOXIPHEN-LIKE →

FIG.20

COMPOSITIONS AND METHODS FOR DETECTING LIGAND-DEPENDENT NUCLEAR RECEPTOR AND COACTIVATOR INTERACTIONS

TECHNICAL FIELD

The invention relates to the fields of molecular genetics and pharmacology. The invention provides methods and compositions for determining the capability of a compound, a macromolecular species, or of a stimulatory effector to produce a conformational change in a predetermined nuclear receptor and/or its accessory protein(s), typically to agonize or antagonize a ligand-induced activation of the nuclear receptor. An aspect of the invention can provide a means for identifying agents which are pharmacological agonists or antagonists for one or more predetermined nuclear receptor species. An aspect of the invention relates to a method of rank-ordering a set of compounds with respect to each compound's ability to affect an interaction between one or more nuclear receptor species and a plurality of coactivator and/or corepressor species or similar interfaces; the rank-ordering provides a dataset for identifying pharmacologically active agonists, antagonists, partial agonists, potentiators, and the like.

BACKGROUND OF THE INVENTION

A variety of nuclear receptors exist in animal cells and generally function to effectuate transcriptional regulation on one or more subsets of regulable genes. Most often, the nuclear receptor exhibits a high-affinity binding interaction with one or more species of hydrophobic ligand. These ligand binding interactions can produce a conformational change in the nuclear receptor. The conformational change induced by ligand binding modifies the ability of the nuclear receptor to interact with certain specific receptor-binding DNA sequences and/or to interact with other nuclear proteins (e.g., transcription factors, coactivators, corepressors), so as to modulate the transcription of genes having the specific receptor-binding DNA sequence(s) located so as to influence the transcription of the gene. In one model of steroid receptor action, a ligand-induced conformational change in a ligand-binding domain unmasks a DNA-binding activity in another structural domain of the steroid receptor protein. In the absence of this ligand-induced conformational change, the ligand-binding domain represses the DNA binding activity of the linked structural domain. It has been recently shown that one or more superfamily of proteins, termed "coactivators", and "corepressors", respectively interact with nuclear receptors in a ligand-dependent fashion so as to effect transcriptional activation (coactivators) or so as to inhibit or silence transcription (corepressors) of genes which are transcriptionally modulated by nuclear receptors.

Nuclear hormone receptors comprise a superfamily of over 40 transcription actors. About half of them are classical receptors for lipophilic ligands such as steroids and vitamins. The nuclear hormone receptor gene superfamily encodes structurally related proteins that regulate transcription of target genes. These macromolecules include receptors for steroid and thyroid hormones, vitamins, retinoids, fatty acids, and other nuclear receptor proteins for which no ligands have been found, so-called "orphan receptors". These receptors have modular domains with readily identifiable structural features and sequence motifs. The DNA-binding domain ("DBD") directs the receptors to bind specific DNA sequences as monomers, homodimers, or heterodimers. The ligand-binding domain ("LBD") responds to binding of the cognate hormone; this domain and the amino terminal domain interact with other transcription factors, and with the coactivators and/or corepressors. Nuclear receptor-specific actions are derived from a combination of diverse elements, including availability of ligand, receptors, and nonreceptor factors; target-site structure; interactions with other proteins, such as the general transcription factors and very importantly with the coactivator and/or corepressor proteins.

The steroid/thyroid hormone receptor superfamily of ligand-activated transcription factors encompasses not only the receptors for steroids, thyroid hormone, retinoids and vitamin D, but also a large number of proteins whose functions and/or ligands are unknown and which are thus termed orphan receptors. This family of transcription factors integrates signals from ligands as well as from signal transduction pathways, resulting in alterations in mRNA and protein expression that are unique to the complex signals received. These nuclear receptors are implicated in the control of a wide range of physiological responses and homeostatic conditions, including cell differentiation, neoplasia, control of cellular metabolism, and neurological function. For a review of the steroid hormone receptor superfamily, see Ribiero R C (1995) Annu. Rev. Med. 46: 443–453.

There has been substantial interest in identifying ligands which interact with nuclear receptors and modulate the biological effects mediated by these nuclear receptors. Such ligands, whether agonistic or antagonistic to natural physiological ligands of the receptors, would serve as candidate pharmaceuticals for controlling the biological effects of nuclear receptor-mediated transcriptional control and the attendant physiological effects produced thereby. Unfortunately, most conventional assays for identifying potential ligands rely upon the use of libraries of radiolabeled compounds which are tested for their binding coefficient (e.g., via Scatchard analysis) to a purified nuclear receptor species. It is difficult and labor-intensive to obtain such libaries of radiolabeled compounds and then screen the library using binding assays. Furthermore, it has been found that a compound's binding constant is not necessarily predictive of its biological activity as a ligand. As a better proxy for ligand function, transcriptional assays have been developed to assay for ligand-induced transcriptional activation of a nuclear receptor as detected by transcription of a reporter sequence operably linked to a nuclear receptor response element and promoter.

Unfortunately, many of the transcriptional responses generated by ligand-activated nuclear receptors can be subtle and are frequently difficult to detect and/or quantify by conventional transcriptional assay procedures, which are relatively insensitive for monitoring expression of genes which are not abundantly transcribed. Furthermore, many of the conventional transcription assay procedures are difficult to perform and entail problematic steps, such as requiring lysis of the cells being assayed. It is desirable to have a method for detecting ligands of predetermined nuclear receptors with high specificity, sensitivity, and selectivity. In particular, methods to reduce readout background noise that can obscure legitimate signals would find great use in the art for identifying novel pharmaceutical agents that are nuclear receptor ligands, as well as providing sensitive assays for detection and quantitation of ligands which are environmental pollutants that activate nuclear receptors (e.g., TCDD).

Moreover, many nuclear receptor ligands, particularly steroids and steroid-like compounds, often exhibit pleiotropic biological effects through nuclear receptors. For example, both estradiol and tamoxiphen bind to the estrogen receptor, but each compound can produce different biological effects and transcriptional profiles (i.e., the set of genes which are transcriptionally modulated by ligand presence) depending upon the tissue and cell-type involved.

Thus, there exists a need in the art for methods to efficiently identify agents which modulate nuclear receptor function. It is important that such methods have the necessary levels of sensitivity and specificity for identifying bona fide nuclear receptor agonists and/or antagonists. The present invention fulfills these and other needs in the art.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

In accordance with the foregoing, in one aspect of the invention are provided methods for identifying agents which are agonists or antagonists for ligand-induced activation of a predetermined nuclear receptor. There are a variety of formats of the invention, and a plurality of formats may be multiplexed sequentially or in parallel to produce a discrimination profile of a test agent in order to categorize the pharmacological nature of the test agent (e.g., agonist, antagonist, partial agonist, mixed agonist/antagonist, etc.), so as to enable dissecting the pleotropic biological effects of nuclear receptor ligands and correlating the individual effects with chemical structure.

Positive Hybrid System: Coactivators

The methods of the invention typically employ a positive hybrid nuclear receptor signal transduction system, which typically comprises an intact eukaryotic host cell, comprising: (1) a LBD-TRX polynucleotide sequence encoding and expressing a ligand-activatable fusion protein (referred to herein as "LBD-TRX") which comprises a ligand binding domain ("LBD") of a predetermined nuclear receptor covalently linked, typically in polypeptide linkage, to a transcriptional activator domain ("AD") or alternatively to a DNA-binding domain ("DBD") of a predetermined transcription factor (generically, AD and DBD are referred to as "TRX" for convenience),(2) a CA-TRX polynucleotide sequence encoding and expressing a coactivator fusion protein (referred to herein as "CA-TRX") which comprises a domain of a nuclear receptor coactivator protein ("CA") capable of binding to said LBD of said predetermined nuclear receptor linked, typically in polypeptide linkage, to a transcriptional activator domain or alternatively to a DNA-binding domain of a predetermined transcription factor (collectively "TRX"), and (3) a reporter polynucleotide sequence comprising, in linear order, a transcriptional regulatory sequence which is responsive to said predetermined transcription factor and a reporter cassette encoding a sequence that confers a signal or detectable phenotype. The TRX components of the LBD-TRX protein and the CA-TRX protein should be functionally complementary; i.e., if the TRX of one fusion is a DBD, the TRX of the other fusion is an AD, and vice versa. Prior to contacting of the system with an agent which is an agonist ligand of the LBD, the transcriptional activity of the LBD-TRX and CA-TRX with respect to the reporter polynucleotide is substantially absent and the system substantially lacks functional expression of an encoded sequence of the reporter polynucleotide. Subsequent to contacting of the system with an agonist agent which produces an activated conformation of the LBD in the LBD-TRX fusion protein, the CA-TRX fusion protein functionally associates forming a LBD-TRX/CA-TRX complex that is transcriptionally active with respect to the reporter polynucleotide, whereupon the reporter cassette can be transcribed and functionally expressed under the control of the transcriptional regulatory sequence. Thus, functional expression of the reporter cassette serves to report whether the system has been contacted with an agent which induced an activated conformation of the LBD. Advantageously, in one variation, the reporter cassette encodes a cell surface reporter protein which can be detected and/or selected for on the basis of its presence on the surface of a cell membrane. In embodiments where the nuclear receptor signal transduction system consists of metabolically active cells having a polynucleotide sequence encoding the LBD-TRX fusion, the CA-TRX fusion, and a reporter polynucleotide sequence, the system is referred to as a CA-TRX reporter cell.

A nuclear receptor signal transduction system of the present invention can be used to evaluate one or more test agents for their ability to activate the LBD of a predetermined nuclear receptor. Typically, the ability to activate the LBD indicates an agonistic activity as referenced to the physiological ligand of the nuclear receptor. In this aspect of the invention, a test agent is applied to a nuclear receptor signal transduction system and incubated for a suitable incubation period anticipated to be substantially sufficient for the agent to transduce a signal to the LBD. After the incubation period, the expression of the reporter cassette is determined by detecting the presence of the reporter. Test agents which produce a statistically significant increase in reporter as compared to background (e.g., placebo) are scored as receptor agonists. In embodiments where the nuclear receptor signal transduction system comprises a metabolically active intact reporter cell, typically a population of reporter cells is contacted with a test agent, and the ability of the test agent to function as a receptor agonist is determined by either the relative expression of detectable reporter above background as compared to a reference population of reporter cells under substantially equivalent conditions in the absence of said test agent. Dose-response data can be generated in this manner using a variety of different concentrations of the test agent.

In a variation, the method may be used to identify antagonists of a predetermined nuclear receptor LBD by determining the ability of a test agent to produce a statistically significant reduction in the expression the reporter by inhibiting the capacity of a unit dose of a predetermined activating ligand of the LBD from producing the amount of expression of the reporter as occurs in the absence of the test agent.

Positive Hybrid System: Corepressors

The invention can also employ a composition and method for identifying ligands which induce binding of a corepressor to the LBD. These systems typically employ a positive hybrid nuclear receptor signal transduction system (a "CR-TRX" system), which typically comprises an intact eukaryotic host cell, comprising: (1) a LBD-TRX polynucleotide sequence encoding and expressing a ligand-activatable fusion protein (referred to herein as "LBD-TRX") which comprises a ligand binding domain ("LBD") of a predetermined nuclear receptor covalently linked, typically in polypeptide linkage, to a transcriptional activator domain ("AD") or alternatively to a DNA-binding domain ("DBD") of a predetermined transcription factor (generically, AD and DBD are referred to as "TRX" for convenience),(2) a CR-TRX polynucleotide sequence encoding and expressing a corepressor fusion protein (referred to herein as "CR-TRX") which comprises a domain of a nuclear receptor corepressor protein ("CR") capable of binding to said LBD of said predetermined nuclear receptor linked, typically in polypeptide linkage, to a transcriptional activator domain or alternatively to a DNA-binding domain of a predetermined transcription factor (collectively "TRX"), and (3) a reporter polynucleotide sequence comprising, in linear order, a transcriptional regulatory sequence which is responsive to said predetermined transcription factor and a reporter cassette encoding a sequence that confers a signal or detectable phenotype. The TRX components of the LBD-TRX protein and the CR-TRX protein should be functionally complementary; i.e., if the TRX of one fusion is a DBD, the TRX of the other fusion is an AD, and vice versa. Prior to contacting of the system with an agent which is an angonoist ligand of the LBD, the transcriptional activity of the LBD-TRX and CR-TRX with respect to the reporter polynucleotide is substantially absent and the system substantially lacks functional expression of an encoded sequence of the reporter polynucleotide. Subsequent to contacting of the system with an antagonist agent which produces an activated conformation of the LBD in the LBD-TRX fusion protein, the CR-TRX fusion protein functionally associates forming a LBD-TRX/CR-TRX complex that is transcriptionally active with respect to the reporter polynucleotide, whereupon the reporter cassette can be transcribed and functionally expressed under the control of the transcriptional regulatory sequence. Thus, functional expression of the reporter cassette serves to report whether the system has been contacted with an agent which induced an activated conformation of the LED. Advantageously, in one variation, the reporter cassette encodes a cell surface reporter protein which can be detected and/or selected for on the basis of its presence on the surface of a cell membrane. In embodiments where the nuclear receptor signal transduction system consists of metabolically active cells having a polynucleotide sequence encoding the LBD-TRX fusion, the CR-TRX fusion, and a reporter polynucleotide sequence, the system is referred to as a CR-TRX reporter cell.

A nuclear receptor signal transduction system of the present invention can be used to evaluate one or more test agents for their ability to activate the LBD of a predetermined nuclear receptor and induce corepressor binding. Typically, the ability to activate the LBD in this manner indicates an antagonistic or partial (mixed) antagonistic activity as referenced to a physiological ligand of the nuclear receptor. In this aspect of the invention, a test agent is applied to a CR-TRX system and incubated for a suitable incubation period anticipated to be substantially sufficient for the agent to transduce a signal to the LBD. After the incubation period, the expression of the reporter cassette is determined by detecting the presence of the reporter. Test agents which produce a statistically significant increase in reporter as compared to background (e.g., placebo) are scored as receptor antagonists or partial (mixed) antagonists. In embodiments where the nuclear receptor signal transduction system comprises a metabolically active intact reporter cell, typically a population of reporter cells is contacted with a test agent, and the ability of the test agent to function as a receptor agonist is determined by either the relative expression of detectable reporter above background as compared to a reference population of reporter cells under substantially equivalent conditions in the absence of said test agent. Dose-response data can be generated in this manner using a variety of different concentrations of the test agent.

In a variation, the method may be used to identify agonists or partial (mixed) agonists of a predetermined nuclear receptor LBD by determining the ability of a test agent to produce a statistically significant reduction in the expression of the reporter by inhibiting the capacity of a unit dose of a predetermined antagonist ligand of the LBD from producing the amount of expression of the reporter as occurs in the absence of the test agent.

Reverse Hybrid System:Corepressor

In a variation, the invention provides a nuclear receptor signal transduction system, comprising a "reverse hybrid" reporter host cell containing: (1) an LBD-TRX polynucleotide sequence encoding a fusion protein comprising a ligand-binding domain of a nuclear receptor in polypeptide linkage a DBD or AD of a transcription factor; (2) a CR-TRX polynucleotide sequence encoding and expressing a corepressor fusion protein (referred to herein as "CR-TRX") which comprises a domain of a nuclear receptor corepressor protein ("CR") capable of binding to said LBD of said predetermined nuclear receptor linked, typically in polypeptide linkage, to a transcriptional activator domain or alternatively to a DNA-binding domain of a predetermined transcription factor (TRX), and (3) a relay (or signal inverter) gene encoding a protein which is efficiently expressed as a consequence of the LDB-TRX binding to the CR-TRX as a transcriptionally active complex, and (4) reporter gene comprising, in linear order, a transcriptional regulatory sequence responsive to said transcriptionally active complex, and a reporter cassette encoding a reporter, wherein the reporter gene is efficiently expressed then the product of the relay (or signal inverter) gene is substantially absent and is either poorly expressed or not expressed when the relay (or signal inverter) gene is efficiently expressed. In an aspect, the LBD is a functional portion of a steroid hormone superfamily receptor capable of binding a corepressor protein in the absence of activating ligand and capable of undergoing a stimulus-induced conformational change, such as by binding a known agonistic ligand, so as to reduce or abrogate binding to the corepressor. The reverse hybrid system facilitates identification of test agents that relieve corepressor binding to the LBD.

A reverse hybrid nuclear receptor signal transduction system of the present invention can be used to evaluate one or more test agents for their ability to activate the LBD of a predetermined nuclear receptor by relieving corepressor binding. Typically, the ability to activate the LBD indicates an agonistic activity as referenced to the physiological ligand of the nuclear receptor, however given the pleotropic nature of many nuclear receptor ligands, it is possible that some such agents will be agonistic with respect to certain effects and antagonistic with respect to others. In this aspect of the invention, a test agent is applied to a reverse hybrid nuclear receptor signal transduction system and incubated for a suitable incubation period anticipated to be substantially sufficient for the agent to transduce a signal to the LBD. After the incubation period, the expression of the reporter cassette is determined by detecting the presence of the reporter. Test agents which produce a statistically significant increase in reporter as compared to background (e.g., placebo) are scored as receptor agonists. In embodiments where the reverse hybrid nuclear receptor signal transduction system comprises a metabolically active intact reporter cell, typically a population of reporter cells is contacted with a test agent, and the ability of the test agent to function as a receptor agonist is determined by either the relative expression of detectable reporter above background as compared to a reference population of reporter cells under substantially equivalent conditions in the absence of said test agent. Dose-response data can be generated in this manner using a variety of different concentrations of the test agent.

In a variation, the method may be used to identify antagonists of a predetermined nuclear receptor LBD by determining the ability of a test agent to produce a statistically significant reduction in the expression the reporter by inhibiting the capacity of a unit dose of a predetermined activating ligand of the LBD from producing the amount of expression of the reporter as occurs in the absence of the test agent.

Reverse Hybrid System:Coactivators

In a variation of the reverse hybrid system, a coactivator (CA) domain may be used instead of a corepressor (CR) domain, and the system can be used, for example, to identify agents that inhibit, abrogate, disrupt, dinimish, interfere with, or otherwise antagonize the functional interaction of the LBD and the coactivator domain. Such agents need not necessarily interact with the ligand-binding pocket of the LBD, and, for example, may interact with a binding interface between the coactivator and the LDB, or at other sites. The method may be used to identify functional antagonists of a predetermined nuclear receptor LBD by determining the ability of a test agent to produce a statistically significant reduction or relative inhibition in the expression the reporter by inhibiting the capacity of a unit dose of a predetermined activating ligand of the LBD from producing the amount of expression of the reporter as occurs in the absence of the test agent.

The invention can also be modified to identify agents that modulate, either positively or negatively, binding interactions between an LBD and a coactivator or corepressor without said agents necessarily interacting with a bona fide ligand-binding domain of the LBD. Generally, these formats employ an LBD, or binding portion thereof, which is functionally constitutive (i.e., not ligand-dependent) for binding to a coactivator or corepressor, or a binding fragment thereof. Such constitutive LBD species can be found as natural variants, can be generated by mutagenesis and selection for constitutive function, or can be generated by employing a high-affinity bona fide ligand at high concentration or covalently attached to the ligand binding pocket (e.g., via photoaffinity labelling), or other means known to those skilled in the art. In such systems, the constitutive LBD and coactivator (or corepressor) are used in LBD-TRX and CA-TRX (or CR-TRX) fusions in a reverse hybrid system and agents are screened for their ability to inhibit the constitutive LBD:CA (or LBD:CR) interaction as measured by a positive readout of the reporter gene.

Direct Interaction Methods

In a variation of the invention, direct physical interaction, measured as binding, between a LBD domain and a CA domain (or CR domain) as a consequence of ligand presence can be determined. In an aspect, an LBD domain is immobilized on a capture surface and a soluble, labelled or epitope-tagged CA or CR domain is introduced under aqueous physiological conditions, either in the absence or presence of a known ligand or a test agent. A typical format of the direct method can be an ELISA, for illustration. Agents which produce a ligand-induced binding between the immobilized LBD and the soluble, labelled or epitope-tagged CA (or CR), thereby resulting in the CA (or CR) becoming immobilized on the capture surface and retained following washing of the surface with a rinse solution substantially lacking soluble, labelled or epitope-tagged CA (or CR), and thus retained on the capture surface and detected by suitable means, can be identified as candidate ligands.

In a variation, the CA (or CR) can be immobilized on the capture surface and the LBD can be labelled or epitope-tagged. Epitope-tagged proteins can generally be detected by immunochemical methods using at least one antibody species that is specifically reactive with the epitope.

In a variation, the LBD species (or a multiplicity thereof) is immobilized on the capture surface and the soluble, labelled CA and/or CR species (or a multiplicity of species thereof) can be used to identify ligand-induced binding interactions or ligand-dependent relief of binding interactions between an LBD and a CA or CR (or multiple combinations thereof). In such variations, it is usually preferable to employ distinctive labels or epitope-tags for each species of CA and/or CR, which can provide a basis for discrimination of which specie(s) of CA or CR bind to an LBD species (or a collection of LBD species)based upon unique detection of each label or tag on the capture surface. Vice versa, a CA or CR (or multiple species thereof) can be immobilized on the capture surface and multiple species of uniquely labeled or tagged LBDs may be used. In each case, a test agent can be evaluated for its ability to produce a concentration-dependent binding between LBD and CA or CR species and compared to a parallel reaction lacking agent and/or to a parallel reaction lacking agent and containing a known ligand, either agonist or antagonist. Variations which employ multiple species of LBD are termed "LBD multiplexed" and variations which employ multiple species of CA or CR are termed "CA multiplexed" or "CR multiplexed", respectively. Test agents are categorized based on their effect as an agonist, antagonist, or lack of such effect with respect to each combination of LBD and CA or CR. Concentration dependence and $EC_{50}$ or $IC_{50}$ values can be additional parameters for categorization of a test agent as an agonist or antagonist with regard to a particular end point.

Multiplexing of Formats

The invention employs several formats, such as those just described. These formats can be employed in parallel to provide a multiplexed format assay. A multiplexed format assay of the invention comprises at least two of the following: (1) positive hybrid system:coactivator, (2) positive hybrid system:corepressor, (3) reverse hybrid system:coactivator, (4) reverse hybrid system;corepressor, (5) direct interaction assay, or (6) other art-know assay for identifying and/or quantifying ligand efficacy and/or potency as an antagonist or agonist of nuclear receptors. A preferred multiplex assay is a combination of (1) and (5). Additionally, an individual type of format can be multiplexed with regard to LBD species employed and/or CA or CR species employed (e.g., a positive hybrid system with an estrogen receptor LBD and a second positive hybrid system with a thyroid hormone receptor LBD). Combinations of format-multiplexed and LBD-multiplexed, CA-multiplexed, and/or CR-multiplexed systems and methods can be used in an individual method embodiment to enhance sensitivity and/or selectivity of identification of agonists and antagonists of nuclear receptors.

Specificity of Bioeffect Fingerprinting

In an aspect, the invention provides a method for identifying a candidate pharmaceutical agent from a library of test agents, wherein the candidate pharmaceutical agent has a desired biological effect profile ("bioeffect fingerprint"). The method comprises: (1) performing n (where n is a number greater than 2, preferably greater than 3, and less than 10 billion) distinct assays of the invention individually using each discrete test agent (which may be a mixture) of the library so as to obtain for each individual test agent measurements of at least n biological effects as detected as a ligand-induced conformational change or a binding interaction change in a discrete assay, (2) for each biological effect detected, assigning a score value (binary or quantitative) based upon the detection (or lack thereof) of a ligand-induced conformational change or binding interaction in each assay, separately, to generate a score matrix ("bioeffect fingerprint") for each agent, and (3) to compare each agent's score matrix to an equivalent (i.e., representing the same assays under similar conditions) score matrix for one or more predetermined agonist(s) and/or antagonist(s), and thereby identify agents having score matrices substantially similar to the score matrix(ces) of said predetermined agonist(s) or antagonist(s). The substantial identity determination may be made on the basis of the general knowledge and experience of a skilled practitioner in the art, and/or may made on the basis of a rank-ordering of matrix similarity (i.e., total number of matches), and/or may be made by electronic computation using a trained neural network implementation (e.g., BrainMaker running on a Windows platform trained with data from a plurality of predetermined agonists and/or antagonists in similar assays), or by other means. This method provides identification of novel receptor ligands and their characterization based on bioeffect measurements made using in vitro assays and/or cell culture assays. In general, the predictive value of biological effects in vivo of such a multi-parameter method increase with score matrix size (i.e., score matrixes having at least 5 cells or elements, each representing a distinct assay type, are preferred).

In an aspect, the invention also provides novel polypeptides comprising a binding amino acid sequence that is: (1) non-naturally occurring in a nuclear protein, and (2) predetermined to bind to a nuclear receptor, typically by interaction with a binding interface of a nuclear receptor at which naturally-occurring coactivators and/or corepressors bind. These polypeptides and compositions thereof are candidate antagonists for coactivator or corepressor binding (e.g., competitive inhibitors), can be employed as a CA portion of a CA-TRX fusion or as a CR portion of a CR-TRX fusion for use in assays of the invention, such uses can include commercial sale as reagents, and for other uses apparent to those skilled in the art. Such binding amino acid sequences generally comprise a LXXLL (SEQ ID NO:1) motif (wherein L is leucine and X is any of the conventional amino acids) and include, with regard to the LBD of the human estrogen receptor β, the sequences shown in FIG. 19 (SEQ ID NOS:23–40). The novel polypeptides are generally from 5 to 50,000 amino acids long, most usually from 10 to 500 amino acids long, and may comprise one or multiple species of such binding amino acid sequences, which may be repeated, and the remainder of the polypeptide may contain other naturally occuring sequences (e.g., fusions to known proteins) and/or may contain random, pseudorandom, or defined sequence kernal amino acid sequence(s). Peptidomimetics having structural homology to the novel binding sequences are also provided according to methods known in the art; such peptidomimetics or constrained peptides can provide novel therapeutic drugs to provide agonism or antagonism of one or more nuclear receptor ligands.

In an aspect, the nuclear receptor signal transduction system may comprise a transgenic nonhuman animal having all or some somatic cells which are reporter cells. In this aspect, the transgenic nonhuman animal may be adminstered a test agent which may act indirectly (i.e, other than by binding to the LBD) or as an LBD ligand. Detection of reporter expression at a statistically-significant level in said one or more somatic cell types indicates agonist activity of the test agent. In an embodiment, lymphocytes of said transgenic animal are reporter cells and are collected from said transgenic animal following administration of a test agent to the transgenic animal and a suitable incubation period; the relative abundance of lymphocytes expressing the reporter protein as referenced to lymphocytes from an untreated transgenic animal under similar conditions except lacking administration of the test agent serves to identify the agonistic or antagonistic efficacy, if any, of the test compound for activation of the predetermined nuclear receptor in vivo.

Such compositions, reporter host cells, transgenic nonhuman animals, and kits find use as commercially marketable drug development reagents, sensitive diagnostic detection systems for environmental ligands (e.g., to assay polycyclic aromatic hydrocarbons in a sample by detecting their agonistic action on the Ah nuclear receptor and as reagents to titrate biopotency of a nuclear receptor ligand for preparation of pharmaceutical formulations.

Other features and advantages of the invention will be apparent from the following description of the drawings, preferred embodiments of the invention, the examples, and the claims.

BRIEF DESCRIPTION OF THE FIGURES

FIG. 6 shows a schematic portrayal of LRB-TRX, CA-TRX, and CR-TRX constructs used and the reporter polynucleotide of a two-hybrid system. "Receptor" indicates LBD-TRX, with the LBD exemplified by a genereic nuclear receptor (NR) LBD with bound ligand (L), and the TRX domain represented by the VP16 acidic activation domain (VP16). "Coactivator" indicates a CA-TRX, with exemplary CA species being a portion of the SRC-1 protein, a portion of the CBP protein, or isolated LCD sequences from those proteins, the TRX domain is exemplified as the Gal4 DNA binding domain (DBD). "Corepressor" indicates a CR-TRX, with exemplary CR species being the interacting domains (ID1 or ID2) from SMRT or NcoR fused to the TRX domain as exemplified by Gal4 DNA binding domain (DBD). The reporter polynucleotide is exemplified as a UAS-TK-luciferase reporter containing binding sites for Gal4 DBD. CHO cells were triple transfected with these constructs and hormone added.

FIG. 16 shows the sequences of LacI-fused peptides obtained by screening the library by ERβ panning. The top set of sequences (SEQ ID NOS:3 and 7–17) was obtained from the focused (-LXXLL-) (SEQ ID NO:1) library and the bottom set (SEQ ID NOS:18–22) was obtained from the random sequence (-XXXXX-) (SEQ ID NO:2) library. Notable amino acids are highlighed.

FIG. 19 shows the sequences of the selected clones. Notable amino acid residues are highlighted (SEQ ID NOS:23–40).

FIG. 20 shows a schematic hypothetical example of bioeffect fingerprinting using a two dimensional score matix.

DETAILED DESCRIPTION

Figure 1:
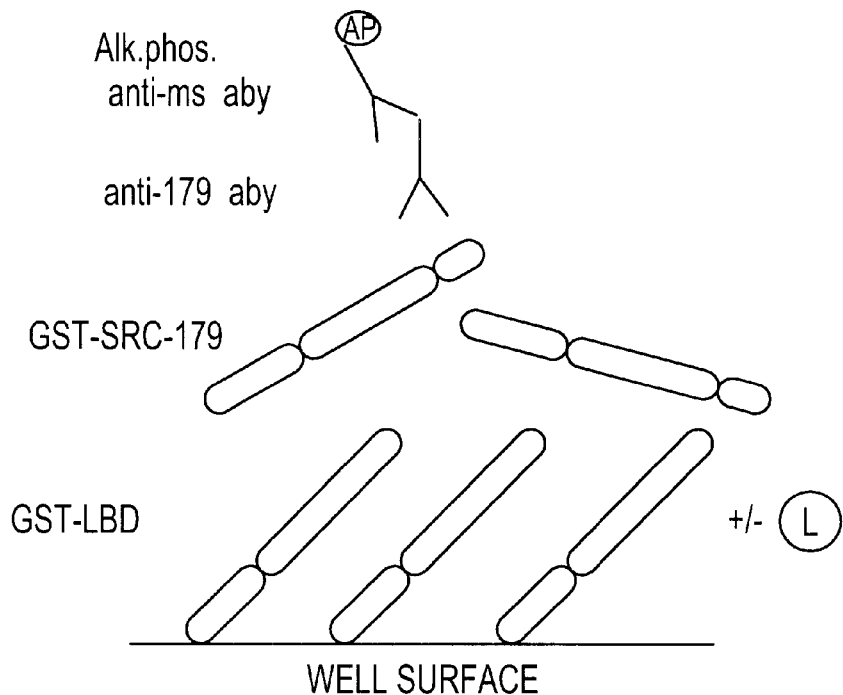
FIG. 1 is a schematic representation of an exemplary embodiment of a direct interaction assay format (ELISA) for measuring interaction of a nuclear receptor LBD with a binding fragment of steroid receptor coactivator-1 (SRC-1). The LBD of the nuclear receptor (ER=estrogen receptor, TRα/β=thryoid hormone receptor α or β form) fused in-frame to a glutathione S-transferase sequence (GST) to form the binding member for the nuclear receptor LBD which is immobilized on a substrate indicated as a well surface, such as by electrostatic binding to a plastic 96-well plate. The coactivator member contains 3 leucine charged domains (LCDs) of SRC-1 fused in-frame to GST/MBP at the amino-terminus and fused in-frame to an antibody 179 epitope tag at the carboxy-terminus. The LCD (SEQ ID NOS:4–6) sequences are shown. The SRC-1 fusion member that is bound to the immobilized LBD is detected with a mouse antibody that specifically reacts with the 179 epitope and a second antibody (alkaline phosphatase conjugated antimouse Ab).

All publications cited herein are incorporated herein in their entirety as if reproduced verbatim.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the term "coactivator" is any limiting factor that enhances the transcriptional activity of a nuclear receptor without substantially altering basal transcription with respect to at least one gene that can be transcriptionally regulated by the nuclear receptor in a ligand-dependent manner, and which binds to the nuclear receptor via direct protein-protein contact(s), typically also in a ligand-dependent or Af-2 domain-dependent manner. Examples of some coactivators include, but are not limited to, SRC-1, ERAP140, RIP140, RIP160, Trip1, SWI1/SNF, ARA70, RAP46, TIF1, CBP, p300, TIF2, GRIP1, TRAP complex proteins, and other such proteins as are known in the art, including those described in Glass et al. (1997) *Curr. Opin. Cell Biol.* 9: 222 or Horwitz et al. (1996) *Mol. Endocrin.* 10: 1167. Coactivators typically contain at least one -LXXLLmotif (LCD), typically at least two or three such motifs. Coactivators typically bind to LBDs in an AF-2 dependent manner. Coactivators can include amino acid sequences which are not found in nature but which are identified by a peptide screening method as binding to a LBD of a nuclear receptor in a ligand-dependent manner.

As used herein the term "corepressor" is any limiting proteinaceous factor that inhibits transcription after being tethered to a promoter by DNA-bound receptors or which blocks binding of a coactivator; factors whose binding to receptors is ligand-regulated; and factors whose inhibitory effect on transcription can be relieved in a ligand-dependent manner. Examples of some corepressors include, but are not limited to, N-Cor, SMRT, calreticulin, TRUP, and Tup1, and other such proteins as are known in the art, including those described in Glass et al. (1997) *Curr. Opin. Cell Biol.* 9: 222 or Horwitz et al. (1996) *Mol. Endocrin.* 10: 1167. Corepressors typically contain at least one or more interaction domains (IDs), typically at least two or three such motifs.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion, but where the remaining amino acid sequence is identical to the corresponding positions in the naturally-occurring (e.g., mature protein) sequence deduced, for example, from a full-length cDNA sequence of a coactivator, corepressor, or nuclear receptor. Fragments typically are at least 14 amino acids long, preferably at least 20 amino acids long, usually at least 50 amino acids long or longer and contain interaction interfaces such as LCDs, IDs, or AF-2.

The term "analog" as used herein refers to polypeptides which are comprised of a segment of at least 25 amino acids that has substantial identity to a portion of an LBD, CA, or CR, and which has specific binding to a nuclear receptor, CA, or CR species. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring polypeptide The term "polypeptide" is used herein as a generic term to refer to native protein, fragments, or analogs of a polypeptide sequence. Hence, native protein, fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

As used herein, the term "LBD" or "ligand-binding domain" refers to the protein domain of a nuclear receptor, such as a steroid superfamily receptor or other suitable nuclear receptor as discussed herein, which binds a physiological ligand (e.g., a steroid hormone) and thereupon undergoes a conformational change and/or altered intermolecular interaction with an associated protein so as to confer a detectable activity upon a second, linked functional domain. When a suitable efficacious ligand interacts with the LBD and forms a liganded complex with an agonist, the LBD is activated and one or more coactivator species become bound. When a suitable efficacious ligand interacts with the LBD and forms a liganded complex with an antagonist, or in some cases in the absence of bound ligand, the LBD binds to one or more corepressor species.

An agonist ligand is defined herein as a ligand which, when bound by the LBD, induces a conformational change and/or alteration of an intermolecular or intermolecular interaction of the LBD so as to induce binding of coactivator and/or dissociation of corepressor. An antagonist ligand is defined herein as a ligand which opposes the effect of an agonist ligand, generally by dose-dependent competitive binding, or by otherwise inducing or stabilizing binding of the LBD to a corepressor or inhibiting LBD binding to one or more coactivator species. Nuclear receptor LBDs are known to and/or can be identified by those skilled in the art and as described herein. Exemplary LBDs are obtained from steroid hormone receptors (e.g., ER, GR, PR, AR, EcR), retinoic acid receptors (e.g., RAR, RXR, RZR), peroxisome proliferator activator receptors (e.g., PPARs), thyroxine (T3) receptor (TR), vitamin D receptor (e.g., VDR), and farsenoid receptor (e.g., FXR), aryl hydrocarbon receptor (Ah) orphan nuclear receptors, among others. The invention is not limited to known nuclear receptors, but can employ LBDs from any suitable nuclear receptor having an LBD which, in the absence of bound ligand, binds corepressor and/or fails to bind coactivator species.

As used herein, the term "LBD-TRX" and "LBD-TRX fusion protein" refer to a polypeptide comprising: (1) a portion of a nuclear receptor (e.g., a steroid receptor superfamily member) which is capable of binding a predetermined ligand species, typically a physiological ligand (e.g., a steroid hormone), with an affinity of at least about $1\times10^{-8}$ M and which, in the absence of bound ligand, can bind corepressor and/or fails to bind one or more coactivator species which can become bound in ligand-dependent manner; and (2) a catalytically active portion of a transcription factor DBD or AD. In some embodiments, a polypeptide spacer of about 1–25 amino acids may separate the LBD portion from the TRX portion. Spacers are preferably non-interfering sequences (i.e., which permit the desired functioning of the LBD-TXR in a cell nucleus), and can be readily determined and selected by the practitioner. In some embodiments, amino-terminal and/or carboxy-terminal extensions of additional amino acids in noninterfering sequences can be present. For typical LBD-TRX species of the invention, the linear order of the LBD and TRX, from amino-terminus to carboxy-terminus, can be varied so lang as the desired function, ligand-inducible activation of binding to coactivator and/or dissociation of corepressor with the LBD-TRX fusion protein, is retained.

As used herein, the term "cell surface reporter" refers to a protein which localizes to the plasma membrane of a host cell and a portion of the protein is exposed to the extracellular region (e.g., an integral membrane protein or a transmembrane glycoprotein, an engineered fusion between a detection protein and a membrane tether sequence), wherein said extracellular portion can be bound by a specific antibody or other ligand with an affinity of at least about $1\times10^{7}$ $M^{-1}$ and/or wherein said extracellular portion can catalyze a detectable conversion of a substrate to a product. The term cell surface reporter also refers to a polynucleotide sequence encoding such a cell surface protein. Various cell surface proteins can be used as cell surface reporters, including fusion proteins comprising at least one segment (e.g., an epitope of at least about 3 consecutive amino acids) that is not present in a naturally-occurring cell surface protein. For example but not limitation, the following may be used as cell surface reporters: a CD (cluster of differentiation) antigen present on cells of a hematopoietic lineage (e.g., CD2, CD4, CD8, CD21, etc.), γ-glutamyltranspeptidase, an adhesion protein (e.g., ICAM-1, ICAM-2, ELAM-1, VCAM-1), spike glycoproteins of enveloped viruses (e.g., glycoprotein H of human cytomegalovirus (hCMV)), and the membrane-bound form of an immunoglobulin μ chain. Also for example but not limitation, a fusion protein between a transmembrane protein and a β-galactosidase protein may compose a cell surface reporter (i.e., a fusion protein having β-galactosidase sequences linked to a γ-glutamyltranspeptidase heavy subunit); cells bearing such fusion proteins can be affinity enriched using an immobilized anti-β-galactosidase antibody. A preferred cell surface reporter protein is a fusion of an enzyme, or a catalytically active portion thereof, to a membrane tether sequence, particularly where the enzyme produces a detectable conversion of substrate to product and wherein the host cell membrane is substantially impermeable to said substrate (e.g., luciferase). Preferably, a cell surface reporter protein is a protein which is not normally expressed at significant levels on the host cells. Since luciferase is an invertebrate protein, fusion proteins comprising luciferase are preferred cell surface reporters for use with mammalian host cells. Numerous other specific examples of suitable cell surface reporters, such, for example, various cloned CD ("cluster of differentiation") antigens, are known to those of skill in the art (e.g., from the literature and GenBank™; such as CD2 GenBank sequence files: Humcd21, Humcd22, Humcd23, Humcd24, and Humcd25, and Muscd21, Muscd22, Muscd23, Muscd24, and Muscd25) and may be selected for use in the methods and polynucleotide constructs of the invention on the basis of the practitioner's desired application.

As used herein, the terms "expression cassette" refers to a polynucleotide comprising a promoter sequence and, optionally, an enhancer and/or silencer element(s), operably linked to a structural sequence, such as a cDNA sequence or genomic DNA sequence. In some embodiments, an expression cassette may also include polyadenylation site sequences to ensure polyadenylation of transcripts. If the encoded protein is to be secreted or retained in the cell membrane, a signal sequence is generally encoded at the amino-terminal portion of the encoding sequence. When an expression cassette is transferred into a suitable host cell, the structural sequence is transcribed from the expression cassette promoter, and a translatable message is generated, either directly or following appropriate RNA splicing. Typically, an expression cassette comprises: (1) a promoter, such as an SV40 early region promoter, HSV tk promoter or phosphoglycerate kinase (pgk) promoter, CMV promoter, Srα promoter or other suitable promoter known in the art, (2) a cloned polynucleotide sequence, such as a cDNA or genomic fragment ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, pcD and λNMT (Okayama H and Berg P (1983) *Mol. Cell. Biol.* 3: 280; Okayama H and Berg P (1985) *Mol. Cell. Biol.* 5: 1136, incorporated herein by reference) or other preferred expression vectors known and available in the art. The transcriptional regulatory sequences in an expression cassette is selected by the practitioner based on the intended application; depending upon the specific use, transcription regulation can employ inducible, repressible, constitutive, cell-type specific, developmental stage-specific, sex-specific, or other desired type of transcriptional regulatory sequence.

As used herein, the term "reporter polynucleotide" refers to a polynucleotide sequence comprising, in linear order, an operably linked transcriptional regulatory sequence and a reporter cassette. In a variation, the reporter polynucleotide encodes a selectable marker which can be selected for in order to ensure the presence of the reporter polynucleotide in the reporter host cells. Preferred selectable marker genes include, but are not limited to, G-418$^R$, mycophenolic acid resistance, DHFR, HSV-tk, and the like. Preferred reporter cassettes include sequences encoding a protein which can be expressed on the cell surface of a metabolically active cell and detected without resulting in non-viability of the cell; preferably such proteins can be readily cleaved from the cell surface if desired so as to reduce background. A reporter polynucleotide may comprise tandem arrays of genetic elements at the discretion of the practitioner.

As used herein, the term "reporter host cell" refers to a eukaryotic cell, preferably a mammalian cell, which harbors a reporter polynucleotide, a LBD-TRX expression cassette, and a CA-TRX expression cassette and/or a CR-TRX expression cassette. The reporter polynucleotide sequence may reside, in polynucleotide linkage, on the same polynucleotide as one or more of the expression cassette sequences, or may reside on a separate polynucleotide. The expression cassettes and/or the reporter polynucleotides may be present as an extrachromosomal element (e.g., replicon), may be integrated into a host cell chromosome, or may be transiently transfected in non-replicable, non-integrated form. Preferably, the expression cassettes and reporter polynucleotide are both stably integrated into a host cell chromosomal location, either by nonhomologous integration or by homologous sequence targeting.

The term "transcriptional modulation" is used herein to refer to the capacity to either enhance transcription or inhibit transcription of a structural sequence linked in cis; such enhancement or inhibition may be contingent on the occurrence of a specific event, such as stimulation with an inducer and/or may only be manifest in certain cell types. For example but not for limitation, expression of a protein that prevents formation of an activated (e.g., ligand-bound) glucocorticoid receptor will alter the ability of a glucocorticoid-responsive cell type to modulate transcription of an glucocorticoid-responsive gene in the presence of glucocorticoid. This alteration will be manifest as an inhibition of the transcriptional enhancement of the glucocorticoid-responsive gene that normally ensues following stimulation with glucocorticoids. The altered ability to modulate transcriptional enhancement or inhibition may affect the inducible transcription of a gene, such as in the just-cited example, or may effect the basal level transcription of a gene, or both. For example, a reporter polynucleotide may comprise a glucocorticoid-inducible enhancer-promoter driving transcription of a sequence encoding a cell surface reporter protein. Such a reporter polypeptide may be transferred to a glucocorticoid-responsive cell line for use as a reporter host cell. Cloned sequences that silence expression of the cell surface reporter in cells cultured in the presence of glucocorticoids also may be (e.g., to reduce basal transcription and ensure detectable glucocorticoid inducibility). Numerous other specific examples of transcription regulatory elements, such as specific enhancers and silencers, are known to those of skill in the art and may be selected for use in the methods and polynucleotide constructs of the invention on the basis of the practitioner's desired application. Literature sources and published patent documents, as well as GenBank™ and other sequence information data sources can be consulted by those of skill in the art in selecting suitable transcription regulatory elements and other structural and functional sequences for use in the invention. Where necessary, a transcription regulatory element may be constructed by synthesis (and ligation, if necessary) of oligonucleotides made on the basis of available sequence information (e.g., GenBank sequences for a CD4 enhancer, HSV-TK promoter, or a SV40 early promoter).

As used herein, "linked" means in polynucleotide linkage (i.e., phosphodiester linkage) or polypeptide linkage, depending upon the context of usage. "Unlinked" means not linked to another polynucleotide or polypeptide sequence; hence, two sequences are unlinked if each sequence has a free 5' terminus and a free 3' terminus.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous. A structural gene (e.g., a HSV tk gene) which is operably linked to a polynucleotide sequence corresponding to a transcriptional regulatory sequence of an endogenous gene is generally expressed in substantially the same temporal and cell type-specific pattern as is the naturally-occurring gene.

Unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As used herein, the term "transcriptional regulatory sequence" refers to a polynucleotide sequence or a polynucleotide segment which, when placed in operable linkage to a transcribable polynucleotide sequence, can produce transcriptional modulation of the operably linked transcribable polynucleotide sequence. A positive transcriptional regulatory element is a DNA sequence which activates transcription alone or in combination with one or more other DNA sequences. Typically, transcriptional regulatory sequences comprise a promoter, frequently an enhancer, and may include other positive and/or negative regulatory elements as are known in the art or as can be readily identified by conventional transcription activity analysis (e.g., with "promoter trap" vectors, transcription rate assays, and the like). Often, transcriptional regulatory sequences include a promoter and a transcription factor recognition site (see, infra). The term often refers to a DNA sequence comprising a functional promoter and any associated transcription elements (e.g., enhancer, CCAAT box, TATA box, SP1 site, etc.) that are essential for transcription of a polynucleotide sequence that is operably linked to the transcription regulatory region.

The term "transcriptional enhancement" is used herein to refer to functional property of producing an increase in the rate of transcription of linked sequences that contain a functional promoter.

As used herein, the term "transcriptional unit" or "transcriptional complex" refers to a polynucleotide sequence that comprises a structural gene (exons), a cares-acting linked promoter and other cares-acting sequences necessary for efficient transcription of the structural sequences, distal regulatory elements necessary for appropriate tissue-specific and developmental transcription of the structural sequences, and additional cares sequences important for efficient transcription and translation (e.g., polyadenylation site, mRNA stability controlling sequences).

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art. For example and not to limit the invention, eukaryotic transcription factors include, but are not limited to: NFAT, AP1, AP-2, Sp1, OCT-1, OCT-2, OAP, NFκB, CREB, CTF, TFIIA, TFIIB, TFIID, Pit-1, C/EBP, SRF (Mitchell P J and Tijan R (1989) Science 245: 371). For purposes of the invention, steroid receptors, steroid superfamily receptors, other nuclear receptors, RNA polymerases, and other proteins that interact with DNA in a sequence-specific manner and exert transcriptional regulatory effects are considered transcription factors.

As used herein, the term "functionally expressed" refers to a coding sequence which is transcribed, translated, post-translationally modified (if relevant), and positioned in a cell such that the protein provides the desired function. With reference to a reporter cassette, functional expression generally means production of a sufficient amount of the encoded cell surface reporter protein to provide a statistically significant detectable signal to report ligand-induced transcriptional effect of a reporter polynucleotide.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as nuclear receptor agonist agents by inclusion in screening assays of the methods described herein or the like. Agents are evaluated for potential activity as specific nuclear receptor agonists by inclusion in screening assays described hereinbelow. Agents may act directly, by serving as a ligand to the LBD of the LBD-TRX fusion protein, and/or they may act indirectly, by producing a second messenger which activates the LBD (e.g., a kinase which phosphorlates the LBD, a second hormone which is a ligand of the LBD, and the like). A "test agent" is an agent which is being evaluated by the methods of the invention to determine whether is possesses agonist activity, antagonist activity, or no activity with regard to the LBD of the nuclear receptor.

As used herein, the term "test ligand" is an agent which has chemical properties consistent with the agent serving as a ligand of a predetermined nuclear receptor LBD with an affinity of at least about $1 \times 10^6$ $M^{-1}$. Typically, these properties can include small size (e.g., MW less than 3,000 Daltons), hydrophobicity, structural similarity to known ligands of the receptor LBD, and/or predicted interaction with an LBD binding pocket based on computer modeling.

As used herein, the term "agonist" refers to an agent which produces activation of a nuclear receptor and/or which, when contacted with a nuclear receptor signal transduction system of the invention, produces a substantial increase in binding of one or more coactivator protein(s) to an LBD-TRX fusion protein, and/or relieves binding of one or more corepressors to the LBD-TRX fusion protein.

As used herein, the term "antagonist" refers to an agent which opposes the agonist activity of a known agonist of the nuclear receptor LBD, or enhances or stabilizes binding of a corepressor protein to a LBD-TRX protein and/or inhibits binding of one or more coactivators to the LBD-TRX fusion protein.

"Physiological conditions" as used herein refers to temperature, pH, ionic strength, viscosity, and like biochemical parameters that are compatible with a viable organism, and/or that typically exist intracellularly in a viable cultured mammalian cell, particularly conditions existing in the nucleus of said mammalian cell. For example, the intranuclear or cytoplasmic conditions in a mammalian cell grown under typical laboratory culture conditions are physiological conditions. Suitable in vitro reaction conditions for in vitro transcription cocktails are generally physiological conditions, and may be exemplified by a variety of art-known nuclear extracts. In general, in vitro physiological conditions can comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s), metal chelators, nonionic detergents, membrane fractions, antifoam agents, and/or scintillants.

As used herein, the terms "label" or "labeled" refer to incorporation of a detectable marker, e.g., a radiolabeled amino acid or a recoverable label (e.g. biotinyl moieties that can be recovered by avidin or streptavidin) or an epitope tag or lined catalytic activity. Recoverable labels can include covalently linked polynucleobase sequences that can be recovered by hybridization to a complementary sequence polynucleotide. Various methods of labeling polypeptides and polynucleotides are known in the art and may be used. Examples of labels include, but are not limited to, the following: radioisotopes (e.g., $^3H$, $^{14}C$, $^{35}S$, $^{125}I$, $^{131}I$), fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for antibodies, transcriptional activator polypeptide, metal binding domains, epitope tags). In some embodiments, labels are attached by spacer arms of various lengths, e.g., to reduce potential steric hindrance. A "labeled antibody" can be a primary antibody having an attached detectable label or a primary antibody which can be detected by a secondary antibody having an attached detectable label.

As used herein, the term "statistically significant" means a result (i.e., an assay readout) that generally is at least two standard deviations above or below the mean of at least three separate determinations of a control assay readout and/or that is statistically significant as determined by Student's t-test or other art-accepted measure of statistical significance.

DESCRIPTION OF THE PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document, as well as: Maniatis et al., *Molecular Cloning: A Laboratory Manual* (1989), 2nd Ed., Cold Spring Harbor, N.Y.; and Berger and Kimmel, *Methods in Enzymology, Volume* 152, *Guide to Molecular Cloning Techniques* (1987), Academic Press, Inc., San Diego, Calif., which are incorporated herein by reference. The procedures are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

All sequences referred to herein by GenBank database file designation (e.g., GenBank: Humatct4a) or otherwise obtainable by routine search of a publicly-available sequence dtabase or scientific publications and are incorporated herein by reference and are publicly available, such as by reconstruction of the sequence by overlapping oligonucleotides or other means.

All publications referred to are incorporated herein for all purposes, including as if the publications, including any diagrams or figures, were reproduced herein.

Overview

In general, the invention encompasses methods, polynucleotide constructs, and host cells which are employed for generating and screening agents for the purpose of identifying agents which are agonists or antagonists of a predetermined nuclear receptor having a LBD which can, in a first state unbound by agonist ligand, remain substantially unbound with regard to a coactivator protein, typically a protein containing at least one -LXXLL- motif, and, in a second state bound by agonist ligand, bind to said coactivator protein. In general, the methods employ a LBD-TRX fusion protein to detect agonist ligands. Agonist ligands produce a conformational change in the LBD-TRX, thereby activating a binding moiety that allows binding to a coactivator protein (or dissociation of a corepressor protein), said binding moiety which is otherwise substantially repressed by the unliganded LBD. The result of the ligand-induced LBD alteration causes binding of a CA-TRX to form a transcriptionally active complex which can drive transcription of the reporter polynucleotide to produce functional expression of the reporter cassette.

The invention separates the function of ligand binding from other functions of transcription factors, coupling ligand binding to cofactor-binding activity which can be assessed by a particularly advantageous means of measuring these inter-protein interactions.

Wagner et al. (1998) *Mol. Cell. Biol.* 18: 1369, Horwitz (1996) op.cit, Glass et al. (1997) op.cit, and Krey et al. (1997) *Mol. Endocrin.* 35: 779, describe methods for identifying LBD interactions with coactivators and corepressors in a ligand-dependent manner.

The present invention provides methods and compositions provide a means for highly sensitive, reliable, and automatable screening a bank of agents to identify agonist agents and antagonists which are able to conformationally activate the LBD of a nuclear receptor.

Nuclear Receptor LBDs

Nuclear receptors suitable for providing an LBD for the method are those receptors which are localized in the nucleus and/or can translocate to the nucleus upon ligand binding. Such nuclear receptors which have a regulable domain which represses an adjacent, or closely linked, functional domain, wherein such repression is substantially relieved upon activation of the regulable domain by an agonistic stimulus, such as by binding of an agonist ligand, are suitable for use. Often, the regulable domain binds a known ligand, such as a steroid hormone, retinoid, or other generally hydrophobic small molecule ligand. Most usually, ligand binding and domain activation occurs in a stereospecific manner which is selective for particular ligand geometries and structural features. Ribiero R C et al. (1995) op.cit provides a general overview of some such nuclear receptors. Glass et al. (1997) op.cit also provides examples of nuclear receptors.

The list of known nuclear receptors includes, but is not limited to the steroid receptor superfamily (e.g., estrogen receptor (ER), progesterone receptor (PR), androgen receptor (AR), glucocorticoid receptor (GR), retinoic acid receptor ("RAR"), retinoid-X receptor ("RXR"), vitamin D receptor ("VDR"),peroxisome proliferator activation receptor ("PPAR"; such as for example PPARα, PPARγ, and PPARδ), thyroid hormone receptor ("TR"), farnesoid receptor ("FXR"), insect ecdysone receptor ("EcR"), retinoid-Z receptor ("RZR" ), and other related receptor homolog genes as is known in the art and/or can be determined by a skilled artisan by computerized homology searching of public nucleic acid and protein sequence databases. Green et al (1995) *Mutat. Res.* 333:101 discloses the peroxisome proliferator activation receptor (PPAR). Greiner et al. (1996) *PNAS* 93:10105, Carlberg et al. (1994) *Mol. Endocrinol.* 8:757, Medvedev et al. (1996) *Gene* 181:199, and Schrader et al. (1996) *J. Biol. Chem.* 271:19732, disclose the RZR receptor. Kephart et al. (1996) *Mol. Endocrinol.* 10:408 discloses the vitamin D receptors (VDRs). Kozak et al. (1996) *Mamm. Genome* 7:164 discloses the farsenoid receptor (FXR). The sequences of the steroid receptor superfamily members can be readily obtained from public sequence databases and published scientific and patent literature. The identification of the ligand binding domain (LBD) for each member is either published or can be determined by a skilled artisan on the basis of sequence identity and structural homology to known steroid superfamily receptors. Routine assay to determine the exact boundaries, if necessary, of the LBD of a given nuclear receptor can be performed by straightforward deletion analysis and measurement of ligand binding and/or retention of a fragment to confer ligand-induced derepression of a linked SSR.

LBD-TRX Fusion Proteins

Polypeptides encoding LBD-TRX fusion proteins which are ligand-activable transcription partners with complementing hybrid CA-TRX or CR-TRX fusion proteins can be expressed from a polynucleotide encoding a protein comprising a LBD of a nuclear receptor in polypeptide linkage to a TRX, optionally separated by a polypeptide spacer of from 1 to about 25 amino acids of a non-interfering sequence.

In aspects of the invention, the LBD portion of the LBD-TRX fusion protein is a mutein comprising at least one mutation as compared to the LBD sequence of the naturally occurring nuclear receptor from which the LED was derived.

Kellendonk et al. (1996) *Nucleic Acids Res.* 24:1404, Zhang et al. (1996) *Nucleic Acids Res.* 24:543, and Metzger et al. (1995) *PNAS* 92:6991, report fusions of hormone-binding domains to Cre recombinase to produce a hormone-inducible Cre recombinase. Logie C and Stewart A F (1995) op.cit. Report fusion of a hormone-responsive domain to FLP recombinase. Kolb A F and Siddell S G (1996) *Gene* 183:1 also report enzymatically active fusions of the Cre recombinase. Thus, skilled artisans are able to identify suitable portions of nuclear receptors for obtaining the necessary encoding segments for the LBD portions of a LBD-TRX. For convenience, practitioners can refer to such publications for additional guidance in selecting LBD sequences.

Reporter Polynucleotides

A reporter polynucleotide unit comprises a transcriptional regulatory sequence operably linked to a structural sequence that encodes reporter. The reporter polynucleotide may comprise one or more tandem repeats of this basic format, so as to amplify the signal-to-noise ratio in cells in which a LBD-TRX is activated by ligand. In a variation, at least two repeats of the reporter polynucleotide unit are present and linked by a spacer sufficient to reduce the frequency of inter-unit site-specific recombination which could reduce signal. A sufficient space is believed to be about at least 100 to 250 nucleotides of non-interfering sequence, and can be readily calibrated empirically by varying the lengths of spacer polynucleotide sequence and determining optimal lengths for maximal reporter gene expression. Spacers of less than 100 nucleotides or more than 250 nucleotides can be used at the discretion of the practitioner. The reporter polynucleotide may be linked to the LBD-TRX (CA-TRX and/or CR-TRX) expression cassette or it may be unlinked.

Reporter Proteins

The reporter genes used in the art include the conventional reporters of transcription (e.g., β-gal, luciferase, chloramphenicol acetyltransferase (CAT), selectable drug markers (neo, gpt, tk), alkaline phosphatase, and green fluorescent protein).

Reporter enzymes can be natural full-length proteins or enzymatically functional fragments and amino acid sequence variants of the such. For example, some enzymes have a single domain that in isolation can confer enzymatic activity. Suitable reporter genes for use in the invention include chloramphenicol acetyl transferase (CAT) (Alton & Vapnek (1979), *Nature* 282:864–869); luciferase (luc); alkaline phosphatase (Toh et al. (1989), *Eur. J. Biochem.* 182:231–238); and β-galactosidase. Firefly luciferase is particularly suitable (deWet (1986) Methods in Enzymology 133:314; de Wet et al. (1985) Proc. Natl. Acad. Sci. 82:7870–7873; deWet et al. (1987) Mol. Cell. Biol. 7:725–737). Four species of firefly from which the DNA encoding luciferase may be derived, are the Japanese GENJI and HEIKE fireflies *Luciola cruciata* and *Luciola lateralis*, the East European Firefly *Luciola mingrelica* and the North American firefly (*Photinus pyralis*) (commercially available from Promega as the plasmid pGEM). The glow-worm *Lampyris noctiluca* is a further source of luciferase gene having 84% sequence identity to that of *Photinus pyralis*. The sequences obtaining reporter enzymes can be genomic, cDNA, a hybrid of the two, or synthetic. The advantages of the present invention are realized most fully for reporter enzymes having substrates to which a eukaryotic cell plasma membrane is substantially impermeable. That is such a substrate is not taken up by such cells in sufficient amounts to generate a readily detectable metabolic product that distinguishes cells expressing a reporter enzyme from other cells. Such is the case for substrates of luciferase, alkaline phosphatase and beta-galactosidase.

One type of reporter protein comprises a sequence of a naturally-occurring cell surface protein (e.g., human CD8, membrane-bound $\mu$ immunoglobulin, glycophorin A) or may be a fusion protein (e.g., a β-galactosidase/γ-glutamyl transpeptidase fusion protein). Preferably, the cell surface reporter protein either is a protein not normally expressed on the host cells or is heterologous (i.e., from a different species), so that the cell surface reporter can be discriminated, for example with a species-specific antibody, from cell surface proteins that naturally occur on the host cell surface. More preferably, the cell surface reporter protein is both heterologous and a protein not normally expressed on the host cell. For example, a mouse hepatoma cell does not normally express a significant amount of CD8 protein, a protein characteristic of cytotoxic T lymphocytes. With reference to the mouse hepatoma cell, a cell surface reporter comprising a human CD8 protein is both heterologous and a protein not normally expressed on the cell type (i.e., hepatocyte). A structural sequence of a cell surface reporter may comprise a polynucleotide sequence encoding a fusion protein having a segment that does not occur naturally in eukaryotes (e.g., a bacterial sequence such as β-galactosidase) fused, in correct reading frame, into an extracellular portion of a transmembrane protein (e.g., human γ-glutamyltranspeptidase heavy subunit; GenBank: Humggt, Humggtx; Goodspeed et al. (1989) *Gene* 76: 1, incorporated herein by reference).

Host cells

Host cells typically include mammalian cells and other types of eukaryotic cells, such as yeast, insect cell, and fungi. Immortalized host cell cultures amenable to transfection and in Vitro cell culture and of the kind typically employed in genetic engineering are preferred (e.g., HeLa cells, KB cells, JW-2 cells, Detroit 6 cells, COS cells, CV-1 cells, VERO cells, and NIH-3T3 cells). Embryonic cell used for generating transgenic animals are also suitable (e.g., zygotes and embryonic stem cells). The cell type should be capable of expressing the reporter construct encoding a fusion protein. Host cells are typically mammalian cells, and most preferably are mammalian cell lines, such as HepG2, COS-7, CHO, HeLa, Hepa, NIH3T3, EBV-immortalized lymphocytes, or other cell lines available in the art. Suitable cell lines and cell strains may be obtained from several sources, including the American Type Culture Collection ("ATCC Catalog of Cell Lines and Hybridomas", American Type Culture Collection, Rockville, Md., which is incorporated herein by reference). Alternatively, it is possible to practice the invention with primary cell explants, such as lymphocytes, hematopoietic stem cells, and primary hepatocytes.

Various host cells may be selected in the discretion of the practitioner. The selection of a host cell generally is based upon the competence of the cell to support transcription from the transcription regulatory sequence of the reporter polynucleotide.

A host cell which harbors a reporter polynucleotide and fusion protein expression cassettes is a reporter host cell. A reporter host cell may harbor the reporter polynucleotide in any of several formats, including: as a replicable episome, as a nonhomologously integrated transgene, as a homologously targeted sequence, as an artificial chromosome, or as a transient non-replicable polynucleotide. A reporter host cell can be readily identified as such by the detectable presence of a reporter polynucleotide, which comprises a transcription regulatory sequence operably linked to a reporter sequence and which, when considered as a unitary polynucleotide sequence spanning both structural and regulatory elements, is not present in the host cell genome as a naturally-occurring polynucleotide sequence.

Specific protein-protein interactions are fundamental to most cellular and organismal functions. Polypeptide interactions are involved in formation of functional transcription complexes, signal transduction pathways, cytoskeletal organization (e.g., microtubule polymerization), polypeptide hormone receptor-ligand binding, organization of multi-subunit enzyme complexes, and the like.

Two-Hybrid Interaction Systems

Investigation of protein-protein interactions under physiological conditions has been problematic. Considerable effort has been made to identify proteins that bind to proteins of interest. Typically, these interactions have been detected by using co-precipitation experiments in which an antibody to a known protein is mixed with a cell extract and used to precipitate the known protein and any proteins which are stably associated with it. This method has several disadvantages, such as: (1) it only detects proteins which are associated in cell extract conditions rather than under physiological, intracellular conditions, (2) it only detects proteins which bind to the known protein with sufficient strength and stability for efficient co-immunoprecipitation, and (3) it fails to detect associated proteins which are displaced from the known protein upon antibody binding. For these reasons and others, improved methods for identifying proteins which interact with a known protein have been developed.

Two-Hybrid Systems

One approach has been to use a so-called "two-hybrid" system to identify polypeptide sequences which bind to a predetermined polypeptide sequence present in a fusion protein (Chien et al. (1991) *Proc. Natl. Acad. Sci.* (*USA*) 88: 9578). This approach identifies protein-protein interactions in vivo through reconstitution of a transcriptional activator (Fields S and Song O (1989) *Nature* 340: 245), the yeast Gal4 transcription protein. The method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site. Typically, the two-hybrid method is used to identify novel polypeptide sequences which interact with a known protein (Silver S C and Hunt S W (1993) *Mol. Biol. Rep.* 17: 155; Durfee et al. (1993) *Genes Devel.* 7; 555; Yang et al. (1992) *Science* 257: 680; Luban et al. (1993) *Cell* 73: 1067; Hardy et al. (1992) *Genes Devel.* 6; 801; Bartel et al. (1993) *Biotechniques* 14: 920; and Vojtek et al. (1993) *Cell* 74: 205). However, variations of the two-hybrid method have been used to identify mutations of a known protein that affect its binding to a second known protein (Li B and Fields S (1993) *FASEB J.* 7: 957; Lalo et al. (1993) *Proc. Natl. Acad. Sci.* (*USA*) 90: 5524; Jackson et al. (1993) *Mol. Cell. Biol.* 13; 2899; and Madura et al. (1993) *J. Biol. Chem.* 268: 12046). Two-hybrid systems have also been used to identify interacting structural domains of two known proteins (Bardwell et al. (1993) *med. Microbiol.* 8: 1177; Chakraborty et al. (1992) *J. Biol. Chem.* 267: 17498; Staudinger et al. (1993) *J. Biol. Chem.* 268: 4608; and Milne G T and Weaver D T (1993) *Genes Devel.* 7; 1755) or domains responsible for oligomerization of a single protein (Iwabuchi et al. (1993) *Oncogene* 8; 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci.* (*USA*) 89: 4159). Alternatively, an *E. coli*/BCCP interactive screening system (Germino et al. (1993) *Proc. Natl. Acad. Sci.* (*U.S.A.*) 90: 933; Guarente L (1993) *Proc. Natl. Acad. Sci.* (*U.S.A.*) 90: 1639) can be used to identify interacting protein sequences (i.e., protein sequences which heterodimerize or form higher order heteromultimers).

Each of these two-hybrid methods rely upon a positive association between two Gal4 fusion proteins thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a calorimetric enzyme assay or (2) as enhanced cell growth on a defined medium (e.g., HIS3). Thus, these methods are suited for identifying a positive interaction of polypeptide sequences, but are poorly suited for identifying agents or conditions which alter (e.g., inhibit) intermolecular association between two polypeptide sequences.

Reverse Two-Hybrid Systems

A general method is provided, referred to herein as a reverse two-hybrid method, wherein agents which disrupt an intermolecular association between two interacting polypeptides (LBD and either a CA or CR domain) thereby generate a selectable and/or detectable readout (e.g., complementation of an auxotrophic phenotype, expression of a detectable reporter molecule, and the like). Typically, a reverse two-hybrid method produces a positive readout under conditions wherein an agent blocks or otherwise inhibits the intermolecular binding of the interacting polypeptides. A positive readout condition is generally identified as one or more of the following detectable conditions: (1) an increased transcription rate of a predetermined reporter gene, (2) an increased concentration or abundance of a polypeptide product encoded by a predetermined reporter gene, typically such as an enzyme which can be readily assayed in vivo, and/or (3) a selectable or otherwise identifiable phenotypic change in an organism (e.g., yeast) harboring the reverse two-hybrid system. Generally, a selectable or otherwise identifiable phenotypic change that characterizes a positive readout condition confers upon the organism either: a selective growth advantage on a defined medium, a mating phenotype, a characteristic morphology or developmental stage, drug resistance, or a detectable enzymatic activity (e.g., β-galactosidase, luciferase, alkaline phosphatase, and the like). In this manner, it is possible to efficiently identify agents (including but not limited to polypeptides, small molecules, and oligonucleotides) which inhibit intermolecular binding between two predetermined interacting polypeptides.

In an aspect of the invention, a reverse two-hybrid system is composed of: (1) a first hybrid protein (e.g., an LBD-TRX), (2) a second hybrid protein (e.g., a CA-TRX or a CR-TRX) which binds to the first hybrid protein under control conditions (e.g., physiological conditions in the absence of agent), (3) a relay (or signal inverter) gene which is efficiently expressed as a consequence of the first hybrid protein and the second hybrid protein being functionally bound to each other, and (4) a reporter gene which is efficiently expressed when the product of the relay (or signal inverter) gene is substantially absent and is either poorly expressed or not expressed when the relay (or signal inverter) gene product is efficiently expressed. The first hybrid protein and second hybrid protein bind to each other through interacting polypeptide segments (i.e., a portion of the first hybrid protein preferentially binds to a portion of the second hybrid protein forming a heterodimer or higher order heteromultimer comprising the first and second hybrid proteins; said binding portions of each hybrid protein are termed "interacting polypeptide segments").

The first hybrid protein comprises: (1) a first interacting polypeptide sequence (LBD) in polypeptide linkage with (2) a DNA-binding domain of a transcriptional activator protein or other DNA binding protein (e.g., a repressor). The second hybrid protein comprises: (1) a second interacting polypeptide sequence (CA or CR), capable of forming an intermolecular association with the first interacting polypeptide sequence under control conditions (e.g., physiological conditions and absence of agent) in polypeptide linkage with (2) an activation domain of a transcriptional activator protein, whereby intermolecular binding between the first hybrid protein and the second hybrid protein (via the interacting polypeptide sequences) thereby unites the DNA-binding domain of the first hybrid protein with the activation domain of the second generating a transcriptional activator function. Generally, the first hybrid protein and the second hybrid protein are encoded by polynucleotides which are constitutively expressed in a host organism (e.g., a eukaryotic or prokaryotic cell, or multicellular organism).

The relay gene (alternatively termed the signal inverter gene) is operably linked to a transcriptional regulatory sequence (a "relay transcriptional regulatory sequence") which is positively regulated by the transcriptional activator that is formed by the intermolecular binding of the first hybrid protein to the second hybrid protein. Hence, when the first hybrid protein binds to the second hybrid protein (via the interacting polypeptide sequences), the transcriptional activator formed thereby binds to a transcriptional regulatory sequence operably linked to the relay gene and enhances the net transcription of the relay gene. The relay gene encodes a protein that represses transcription of a reporter gene. Thus, when the first and second hybrid proteins are functionally bound to each other, the relay gene is expressed and thereby represses transcription of the reporter gene(s). In an embodiment, such relay proteins are of the type often referred to in the art as "negative regulators of transcription". In an embodiment of the invention, the relay gene is a negative regulator of transcription in yeast; for example but not limitation the GAL80 gene can serve as a relay gene in yeast. In embodiments where host organisms are employed to harbor the reverse two-hybrid system, the relay gene is often a gene which naturally occurs in the germline DNA of the host organism species, and frequently can be an endogenous germline gene, or alternatively may be introduced into the host organism as exogenous DNA, typically into a host genome that lacks the corresponding functional endogenous gene (e.g., a "knockout background").

The reporter gene is operably linked to a transcriptional regulatory sequence ("reporter transcriptional regulatory sequence") which is negatively regulated by the gene product of the relay gene and which is induced in the absence of the relay gene product. Thus, transcription of the reporter gene is repressed in control conditions (e.g., physiological conditions in the absence of agent) wherein the two hybrid proteins bind to each other and form a transcriptional activator that increases transcription of the relay gene. Generally, the relay gene product either binds to the transcriptional regulatory sequence operably linked to the reporter gene, or binds to a transcription protein that binds to the transcriptional regulatory sequence operably linked to the reporter gene. The net transcription rate of the reporter gene is reduced (or completely blocked) as a consequence of the relay gene product binding to the reporter gene transcriptional regulatory sequence and/or to a transcription protein required for constitutive expression of the reporter gene. Any of a variety of reporter genes that produce a positive readout can be used. For example and not limitation, suitable reporter genes are those which (1) confer a selectable phenotype to cells in which the reporter gene is efficiently expressed, and/or (2) encode a gene product (e.g., enzyme) which is conveniently detected such as by in situ assay or the like. Suitable genes which confer a selectable phenotype are exemplified by, but not limited to, genes which complement auxotrophic mutations in a host organism (e.g., yeast HIS3), genes which encode drug resistance (e.g., neo$^R$), genes which induce cell proliferation, and other genes whose expression confers a selective growth advantage. Suitable genes which encode a gene product which is conveniently detected in situ are exemplified by, but not limited to, β-galactosidase (e.g., *E. coli* lacZ), luciferase, alkaline phosphatase, horseradish peroxidase, and the like.

The invention provides polynucleotides encoding a first hybrid protein and a second hybrid protein. Such polynucleotides encode a DNA-binding domain or activation domain of a transcriptional activator and conveniently can have a cloning site for adjacent insertion, in reading frame, of polynucleotide sequences encoding one or more interacting polypeptide sequence(s). Typically, a first polynucleotide will encode a first hybrid protein composed of a first predetermined interacting polypeptide sequence and a DNA-binding domain of a transcriptional activator; a second polynucleotide will encode a second hybrid protein composed of a second predetermined interacting polypeptide sequence and an activation domain of a transcriptional activator, wherein the DNA-binding domain of the first hybrid protein can reconstitute with the activation domain and form a functional transcriptional activator. Often, the DNA-binding domain and the activation domain of the hybrid protein pair are derived from the same naturally occurring transcription activator (e.g., Gal4). However, those of skill in the art can select DNA-binding domains and activation domains from distinct transcription activators which can reconstitute to form a functional transcriptional activator which does not occur in nature (e.g., a DNA-binding domain of the bacterial lexA protein can be used in conjunction with a transcriptional activator from the viral protein, VP16; Vojtek et al. (1993) op.cit.). Transcription and translation of such a polynucleotide produces a hybrid (or fusion) protein composed of an interacting polynucleotide segment and a DNA-binding domain or activation domain of a transcriptional activator.

The invention also provides polynucleotides which comprise a transcriptional regulatory sequence operably linked to a relay (or signal inverter) gene A relay (or signal inverter)

gene encodes a protein that inhibits or otherwise represses expression (typically transcription) of a predetermined reporter gene. Most usually, a relay protein is a negative regulator of transcription for a predetermined gene or gene subset. In an embodiment, the relay protein is a transcription repressor protein that binds to a polynucleotide sequence and thereby inhibits transcription of a cis-linked and operably linked sequence. In an alternative embodiment, the relay protein binds to a protein that is a positive regulator of transcription of a predetermined gene or gene subset, and as a consequence of binding thereby inhibits the transcriptional activity of the positive regulator. One variety of such a relay protein binds to and blocks the activation domain(s) of transcriptional activators. Although a variety of suitable relay proteins are apparent to those of skill in the art, this category of relay protein can be exemplified by the mammalian mdm2 oncoprotein which binds the transactivation domain of the tumor suppressor protein p53, and the yeast Gal80 protein which binds and inactivates the activation domain of Gal4. In an embodiment, the relay protein comprises a mutation, addition, or deletion that reduces the stability of the relay protein in vivo as compared to the naturally occurring cognate relay protein. Relay proteins can be referred to as signal inverter proteins, as they serve to invert a positive transcriptional signal (the reconstitution of a functional transcriptional activator by binding of the two hybrid proteins) into a negative transcriptional signal, which reduces transcription of a predetermined reporter gene. Generally, a polynucleotide encoding a relay protein is operably linked to a relay transcriptional regulatory sequence that produces transcription of the relay gene dependent upon functional reconstitution of the DNA-binding domain and activation domain of the two hybrid proteins. For example and not limitation, such a relay transcriptional regulatory sequence can comprise a promoter and a polynucleotide sequence comprising one or more site(s) which bind(s) a reconstituted functional transcriptional activator formed by association of the two hybrid proteins; for example, if the two hybrid transcriptional activator comprises a lexA DNA-binding domain, the relay transcriptional regulatory sequence operably linked to the relay gene can comprise one or more lexA binding site sequences, arrayed in tandem.

Other aspects of two-hybrid systems are described in U.S. Pat. No. 5,525,490, incorporated herein by reference for all purposes.

Other Aspects

The invention provides a method for identifying agonist ligands of a predetermined nuclear receptor. The method comprises:

forming agent-treated host cells by contacting (1) a test agent with (2) a population of reporter cells;

incubating the agent-treated host cell under incubation conditions for a suitable incubation period sufficient for distribution of the test agent to the nucleus to allow for formation, if any, of a liganded complex comprising a LBD-TRX fusion protein and a CA-TRX (or a CR-TRX) fusion protein; and, identifying as an agonist ligand a test agent which produces a statistically significant increase in detectable expression of the reporter protein in the population of agent-treated host cells as compared to a reference population of untreated host cells incubated under substantially identical conditions and lacking said test agent.

In an aspect of the method, the test agent consists of at least one species of small molecule (M.W. <3,000 Daltons). In an aspect of the method, the test agent is a lipophilic compound. In an embodiment, the test agent is a steroid, retinoid, thyroxine analog, vitamin D derivative, or polycyclic aromatic hydrocarbon. In an embodiment, untreated host cells are contacted with vehicle or a known inert substance in place of the test agent. Often, a spacer polypeptide sequence of 1 to about 100 amino acids of a non-interfering amino acid sequence (which may be selected by the artisan and determined empirically without necessitating undue experimentation) is in polypeptide linkage between the LBD segment and the TRX segment and/or between the CA (or CR) segment and its linked TRX segment, such as to reduce potential steric hindrance.

In an aspect, the method may be used to rank-order the efficacy and/or potency (or other pharmacological property) of a collection of test agents for agonist or antagonist activity relative to a predetermined nuclear receptor. A collection (or library) of test agents can be screened, either by parallel screening of individual test agent species or in pools of test agents having related structural features, to determine the ability of each test agent species or pool thereof to elicit a dose-dependent and/or time-dependent activation of the LBD-TRX in a population of reporter host cells. The method typically employs a population of reporter host cells which are subdivided into a plurality of subpopulations that are cultured under substantially identical conditions, such as for example in the wells of a multiwell culture vessel (e.g., 96 well microtitre dish), forming a collection of culture vessels (e.g., wells) each having an approximately equivalent reporter host cell subpopulation exposed to substantially identical conditions. To each culture vessel (e.g., well) is added a predetermined amount or concentration of a test agent or a pool of test agents, such that for a given test agent species or pool, a plurality of dosage levels or concentrations are represented in the collection of culture vessels. For example and not limitation, a 96-well plate may have each row representing a distinct test agent species and each column representing a series of predetermined dosages or concentrations (or predetermined dilution ratios of a stock test agent solution of unknown concentration). Following addition of the test agent or pool, the culture vessels containing the reporter host cells exposed to the test agent or pool are incubated under suitable incubation conditions (e.g., conventional cell culture conditions) for a time period sufficient to produce activation of a nuclear receptor of the type from whence the LBD portion of the LBD-SSR in the reporter host cells was obtained. Following or during the incubation time period, the expression of cell surface reporter protein is detected from each culture vessel and compared to the expression level, if any, of the cell surface reporter in a parallel culture vessel containing reporter host cells cultured under substantially identical conditions but lacking a test agent, but in some embodiments administered the vehicle used to deliver the test agent(s), as a control to establish background reporter expression. If desired, the level of cell surface reporter expression in each culture vessel can be detected and quantified at a plurality of time points, such as to determine a time course of activity for each test agent species or pool. By comparing the amount of cell surface reporter expression in each culture vessel, a dose-response curve (e.g., wherein expression of the cell surface reporter is the response) and/or activation time curve can be calculated for each test agent or pool to determine the pharmacological profile of each test agent or pool. Exemplary pharmacological parameters can include, for example, ED$_{50}$, binding constants, latency of activation, and the like, among others. Each test agent species or pool can be rank-ordered relative to other test agents or pools evaluated under substantially identical conditions on the basis of the dose-response data thus obtained, and preferred test agents having desired pharmacological parameters can be identified thereby.

The invention also provides kits comprising an expression polynucleotide encoding a LBD-SSR fusion, a reporter polynucleotide of the invention, and, optionally, a suitable host cell, and optionally, instructions for use. In a variation, the kit also comprises a second polynucleotide which confers a selectable phenotype on host cells in which said second polynucleotide has undergone site-specific recombination. In an embodiment, the kit comprises reporter cells suitable for use in test agent screening assays to identify agonists and/or antagonists for ligands of the predetermined nuclear receptor.

Although the present invention has been described in some detail by way of illustration for purposes of clarity of understanding, it will be apparent that certain changes and modifications may be practiced within the scope of the claims. The following experimental examples are offered for illustration and are not intended to limit the invention in any way.

EXPERIMENTAL EXAMPLES

Overview

The use of nuclear receptor:coactivator interactions as a means for identifying and categorizing nuclear receptor ligands to be used in high-throughput screening was evaluated. A direct interaction assay suitable for in vitro use with enzymatic readout (ELISA) was constructed using fusion proteins containing TR (thyroid hormone receptor) or ER (estrogen receptor) ligand-binding domains (LBDs) and fragments of the coactivator protein, SRC-1. Specific, ligand-dependent interaction was demonstrated.

Mammalian cell lines containing a two-hybrid system comprising a reporter gene and two hybrid molecules: one containing a nuclear receptor LBD (TR or ER) fused to a VP16 acidic activation domain, and the second containing coactivator protein fragments having at least one leucine-charged domain (LCD) fused to a Gal4 DNA-binding domain, wherein the two hybrids can interact in a ligand-dependent manner leading to reconstitution of transcriptional activity with regard to the reporter gene. The third LCD of SRC-1 was found to be dispensible for interaction with the TRβ and ERβ LBDs, and that the second LCD interacts preferentially with ER rather than TR. In addition, ligand-dependent dissociation of the Trβ LBD from fragments of the corepressor proteins SMRT and NcoR was demonstrated in this format. No detectable interaction between these corepressor fragments and the ERβ LBD was observed in the absence of ligand. Novel peptide motifs which interact with TR and/or ER activator functions in a receptor- and ligand-specific manner. Large random and focused (centered on the leucine charged motif, LXXLL) recombinant peptide diversity libraries were screened and novel sequences which interact specifically with ERβ were identified; estradiol increases the ability of these novel peptides to interact with the ERβ.

EXAMPLE 1

Direct Interaction Assay

Figure 2:
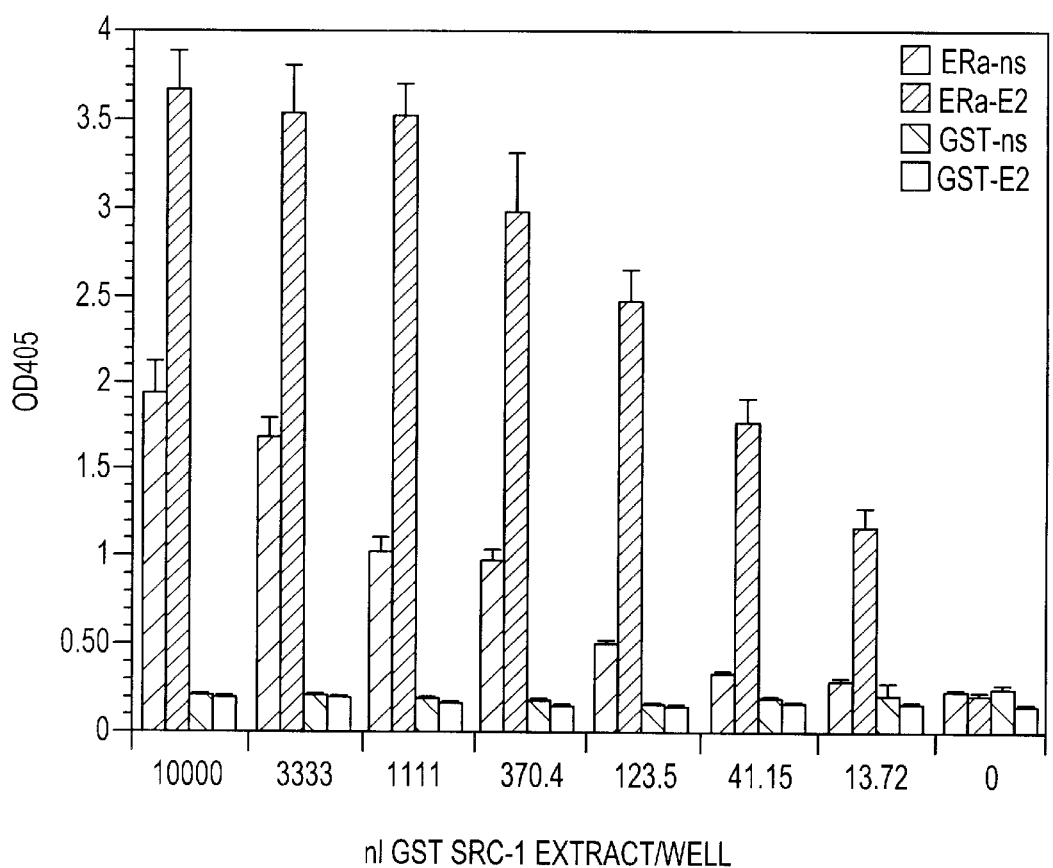
FIG. 2 shows the results of the direct interaction assay using ERα LBD interacting with SRC-1. 0.5 μg of purified GST-ERα was used with varying amounts of crude bacterial lysate containing GST-SRC-1. The interaction is specific (GST control) and enhanced by estradiol.
Figure 3:
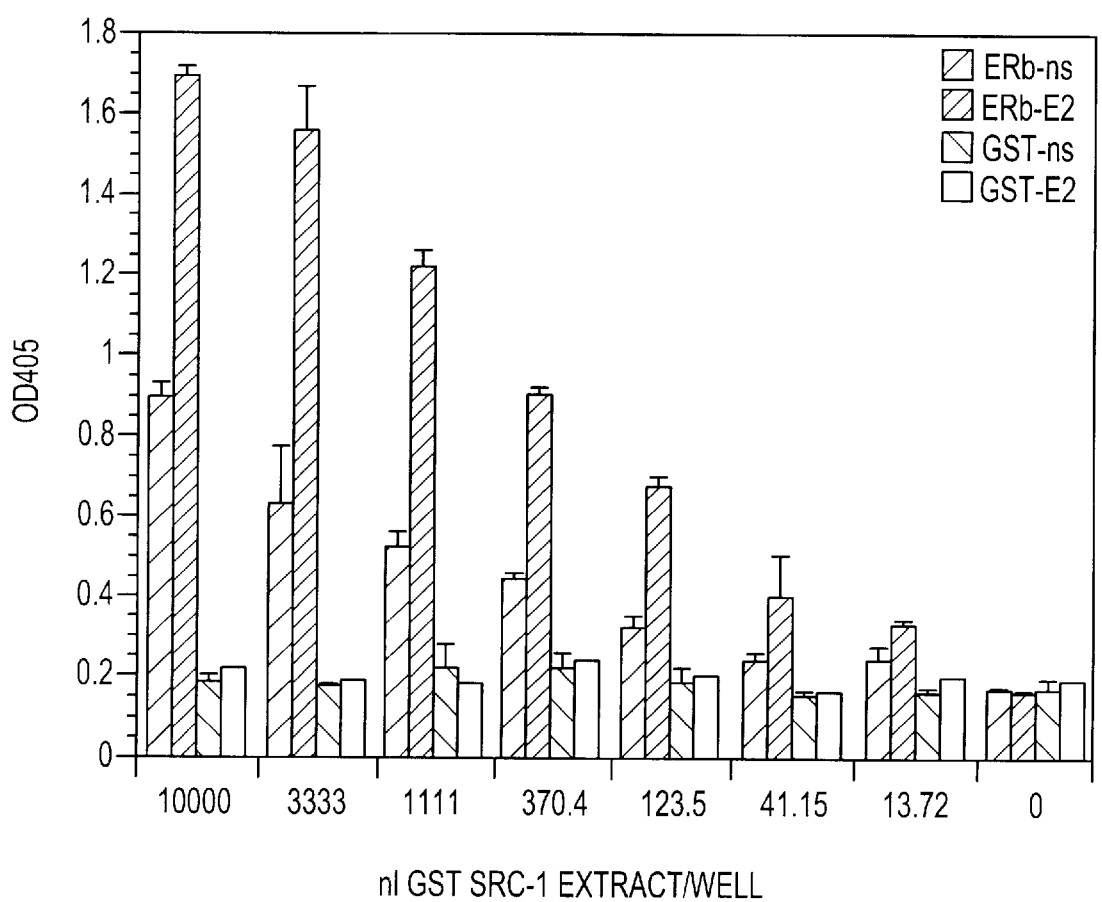
FIG. 3 shows the results of the direct interaction assay using ERβ LBD interacting with SRC-1. 0.5 μg of purified GST-ERβ was used with varying amounts of crude bacterial lysate containing GST-SRC-1. The interaction is specific (GST control) and enhanced by estradiol.
Figure 4:
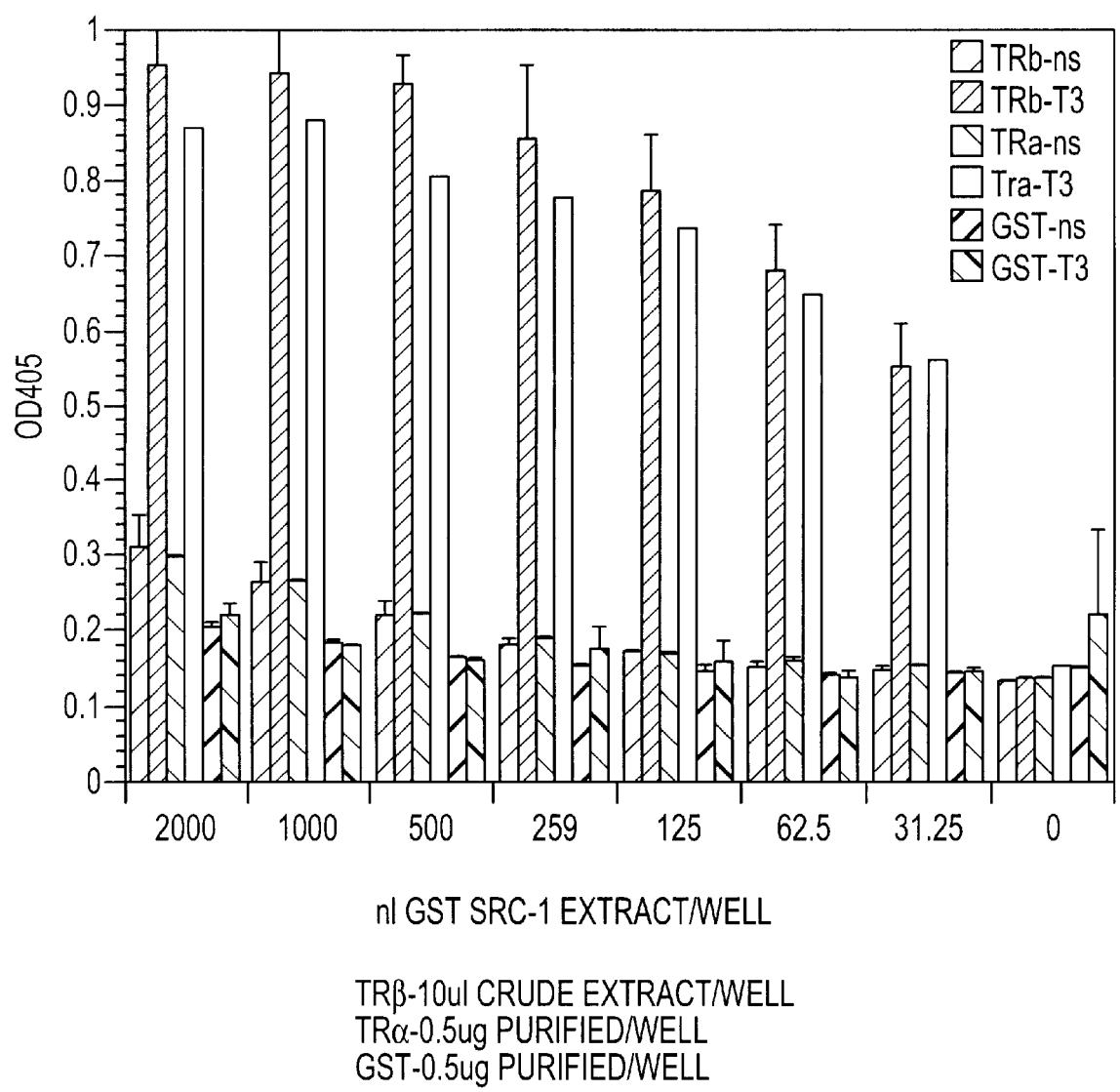
FIG. 4 shows results of a direct interaction assay of the TRβ and TRα LBDs interacting with SRC-1. The indicated amounts of GST fusion proteins were used. The interaction is specific and dependent on T3.
Figure 5:
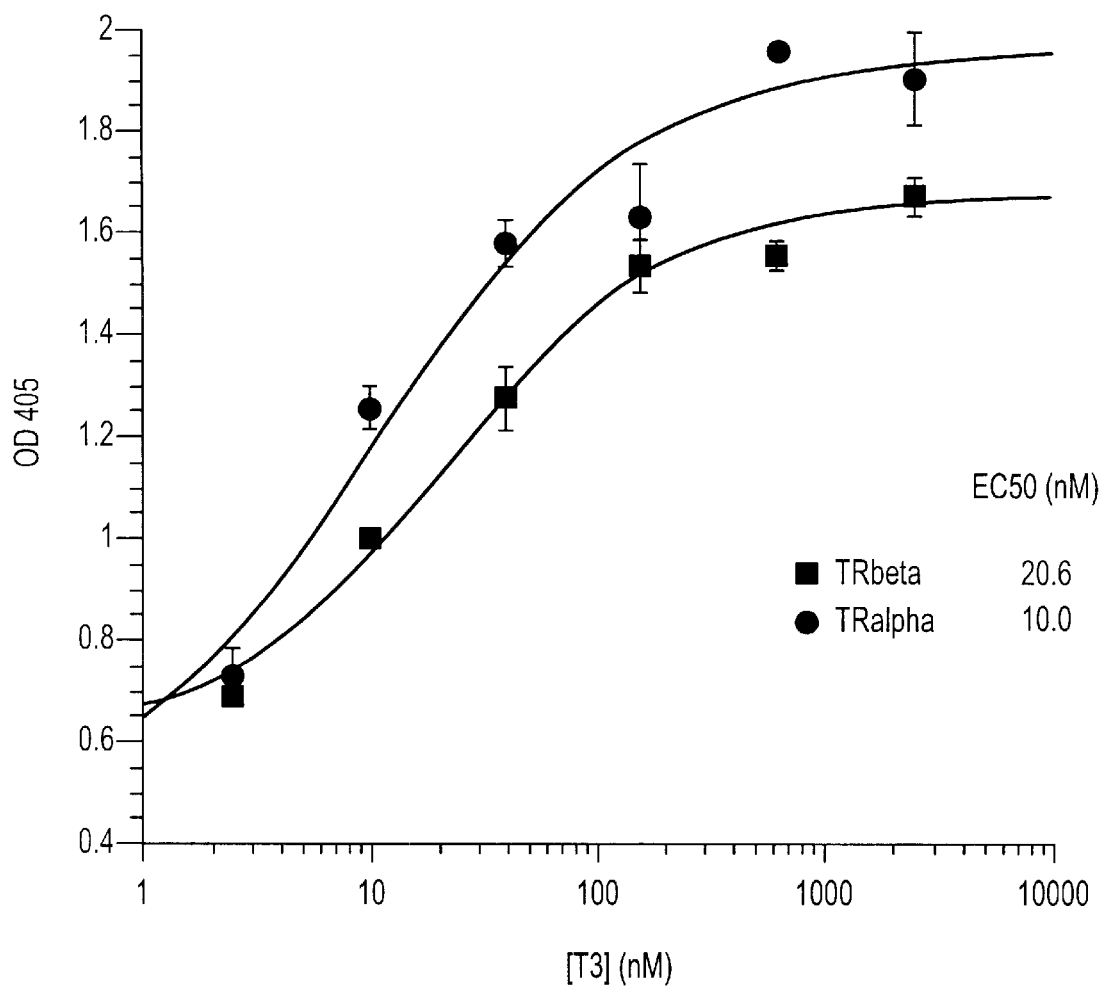
FIG. 5 shows results of a direct interaction assay as a dose-response curve of T3 in promoting interaction between the TRβ and TRα LBDs and SRC-1. T3 appears more potent on the α receptor.

FIG. 1 is a schematic representation of an exemplary embodiment of a direct interaction assay format (ELISA)for measuring interaction of a nuclear receptor LBD with a binding fragment of steroid receptor coactivator-1 (SRC-1). The LBD of the nuclear receptor (ER=estrogen receptor, TRα/β=thryoid hormone receptor α or β form) fused in-frame to a glutathione S-transferase sequence (GST) to form the binding member for the nuclear receptor LBD which is immobilized on a substrate indicated as a well surface, such as by electrostatic binding to a plastic 96-well plate. The coactivator member contains 3 leucine charged domains (LCDs)of SRC-1 fused in-frame to GST/MBP at the amino-terminus and fused in-frame to an antibody 179 epitope tag at the carboxy-terminus. The LCD sequences are shown. The SRC-1 fusion member that is bound to the immobilized LBD is detected with a mouse antibody that specifically reacts with the 179 epitope and a second antibody (alkaline phosphatase conjugated antimouse Ab). FIG. 2 shows the results of the direct interaction assay using ERα LED interacting with SRC-1. 0.5 μg of purified GST-ERα was used with varying amounts of crude bacterial lysate containing GST-SRC-1. The interaction is specific (GST control) and enhanced by estradiol. FIG. 3 shows the results of the direct interaction assay using ERβ LBD interacting with SRC1. 0.5 μg of purified GST-ERβ was used with varying amounts of crude bacterial lysate containing GST-SRC-1. The interaction is specific (GST control) and enhanced by estradiol. FIG. 4 shows results of a direct interaction assay of the TRβ and TRα LBDs interacting with SRC-1. The indicated amounts of GST fusion proteins were used. The interaction is specific and dependent on T3. FIG. 5 shows results of a direct interaction assay as a dose-response curve of T3 in promoting interaction between the TRβ and TRα LBDs and SRC-1. T3 appears more potent on the a receptor.

EXAMPLE 2

Positive Hybrid System:Coactivator

Figure 7:
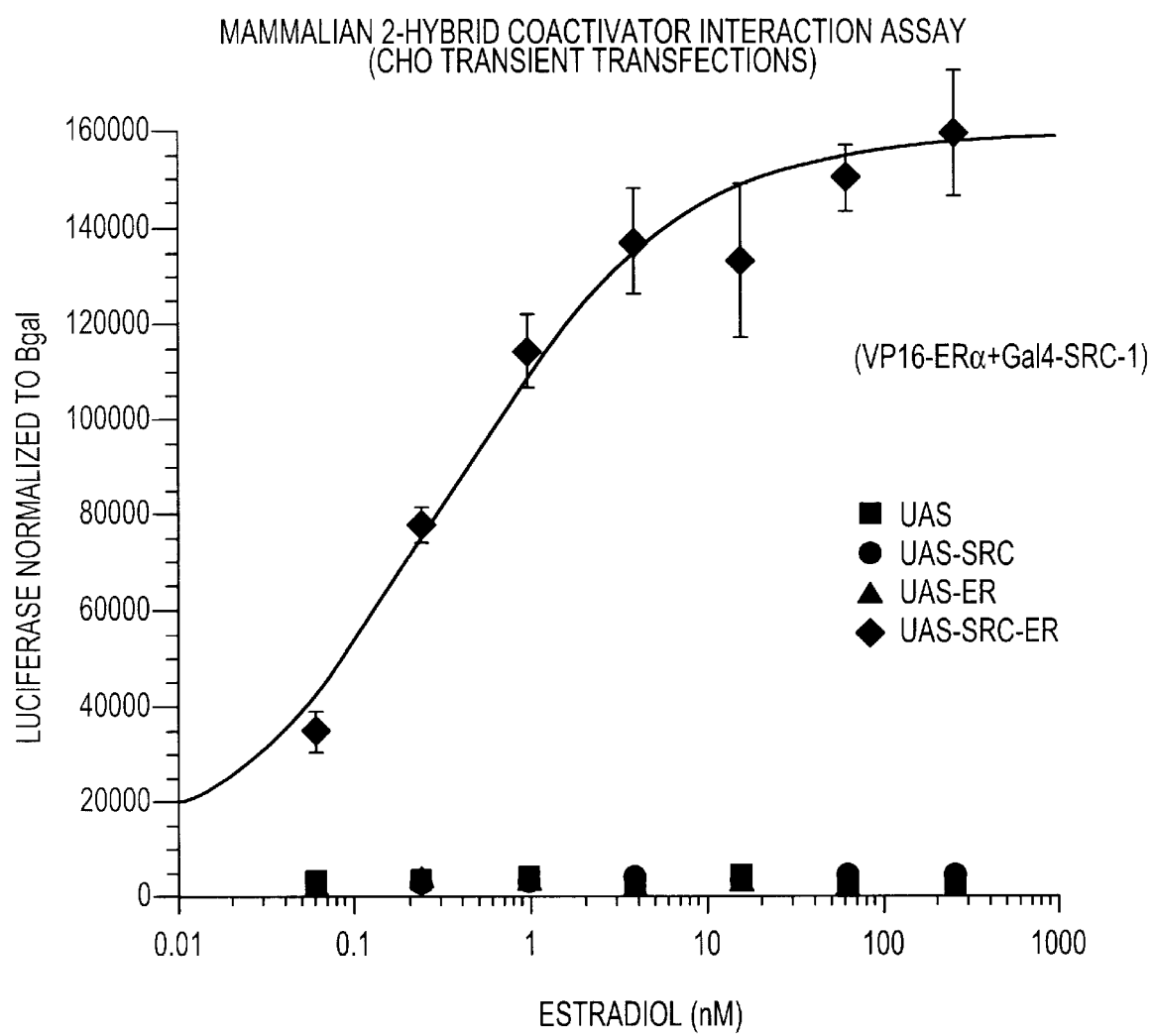
FIG. 7 shows data from a positive two-hybrid system as a dose-response curve showing that reporter (luciferase) is generated only when all three components (VP16ERα, Gal4-SRC-1, and UAS-TK-luciferase) are transfected together, and that the response is dose-dependent with respect to estradiol concentration.
Figure 8:
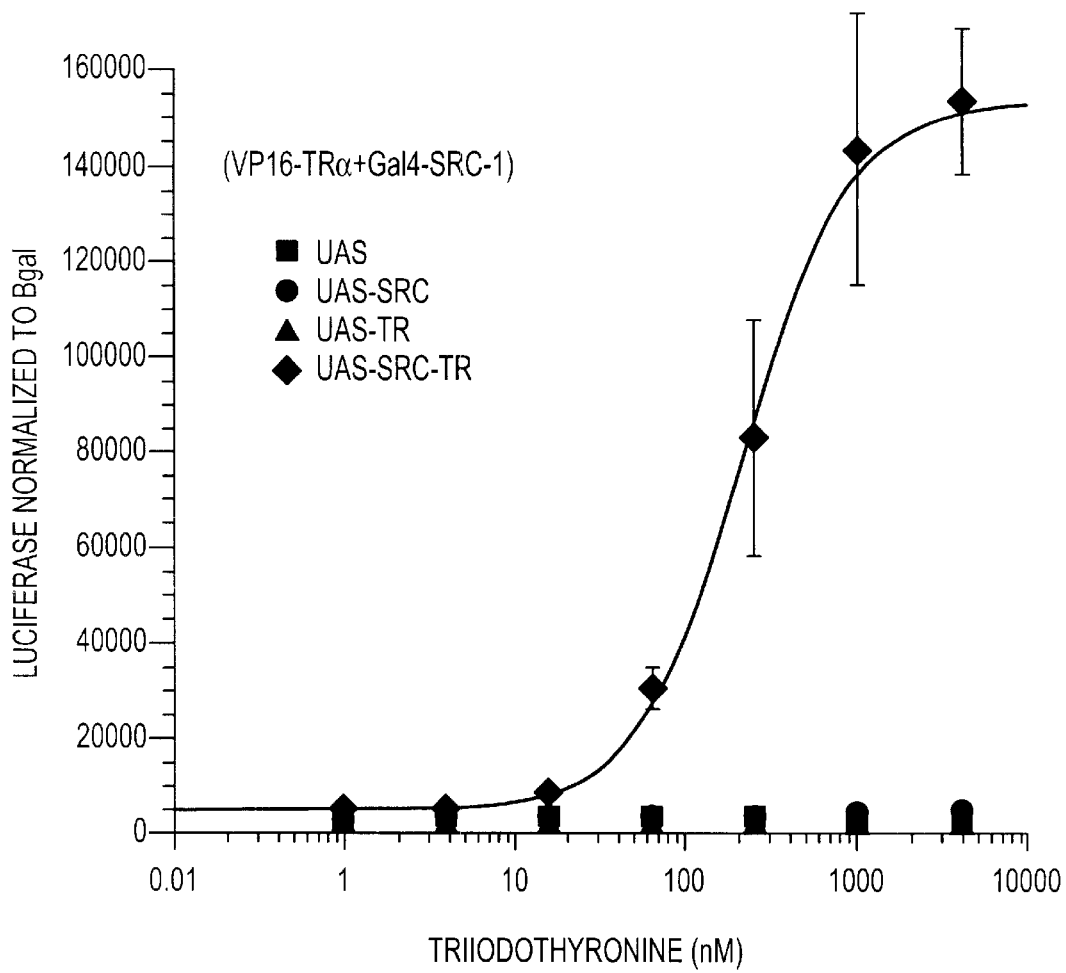
FIG. 8 shows data from a positive two-hybrid system as a dose-response curve showing that reporter (luciferase) is generated only when all three components (VP16TRα, Gal4-SRC-1, and UAS-TK-luciferase) are transfected together, and that the response is dose-dependent with respect to T3 concentration.
Figure 9:
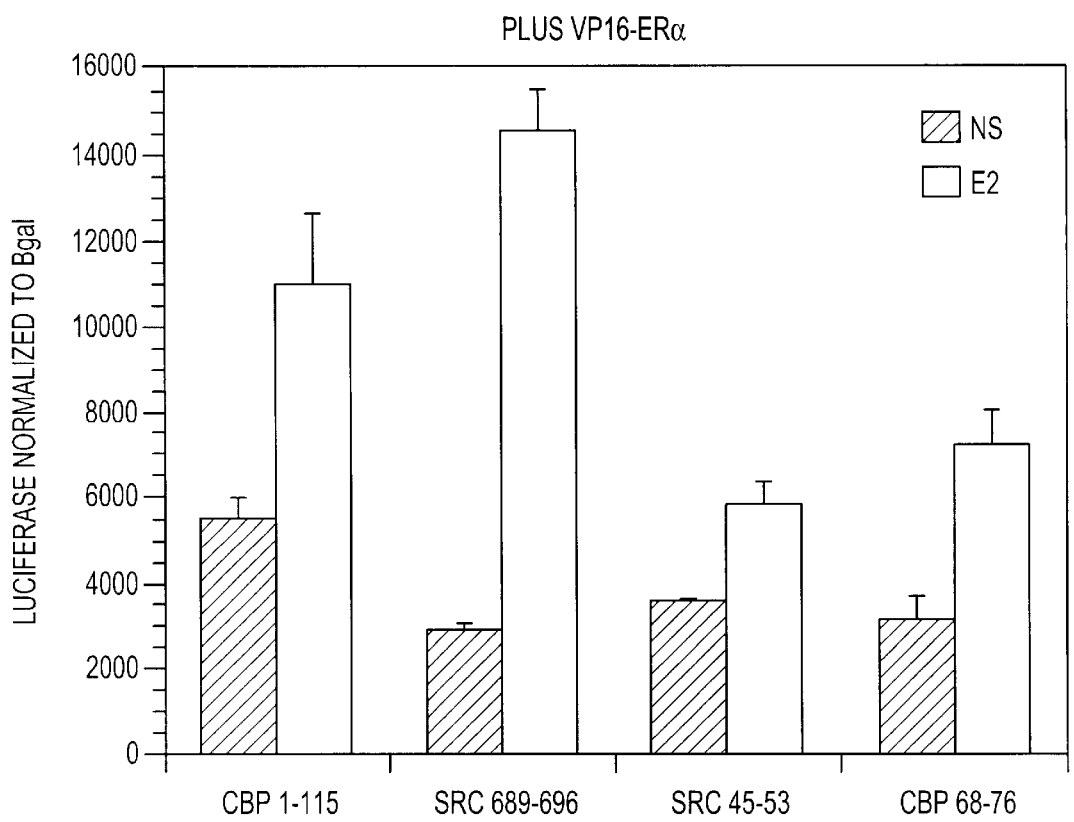
FIG. 9 shows ERα-Vp16 fusions tested against various LCDs in the absence (NS=no steroid present) or presence (E2=estradiol present) of agonistic ERα ligand. Numbers refer to amino acid position of N- and C-termini of fusion portion of coactivator using conventional numbering scheme. SRC 689–696 (LCD #2) appears specific for ERα. Note that these signals are approximately 10-fold lower than with SRC-1 containing 3 LCDs (compare to FIG. 7).
Figure 10:
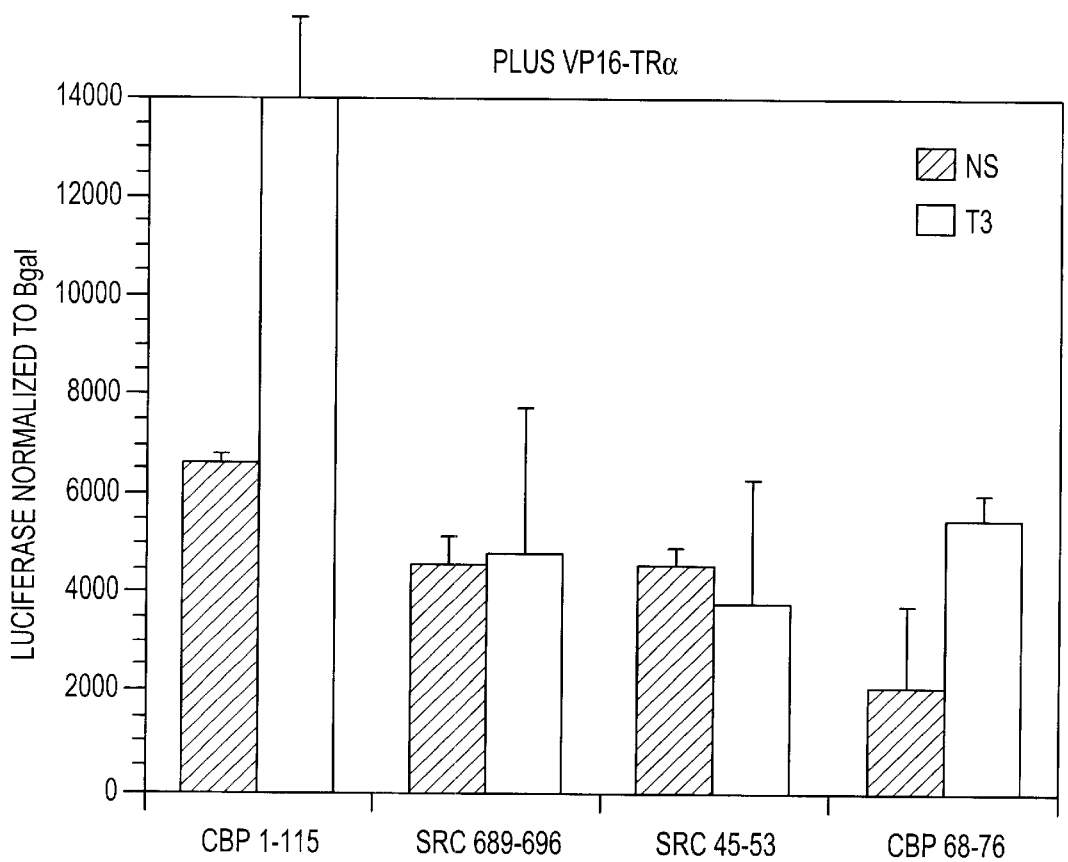
FIG. 10 shows TRα-Vp16 fusions tested against various LCDs in the absence (NS=not stimulated) or presence (T3=triiodothyronine present) of agonistic TRα ligand. Numbers refer to amino acid position of N- and C-termini of fusion portion of coactivator using conventional numbering scheme. Note that these signals are approximately 10-fold lower than with SRC-1 containing 3 LCDs (compare to FIG. 8).
Figure 11:
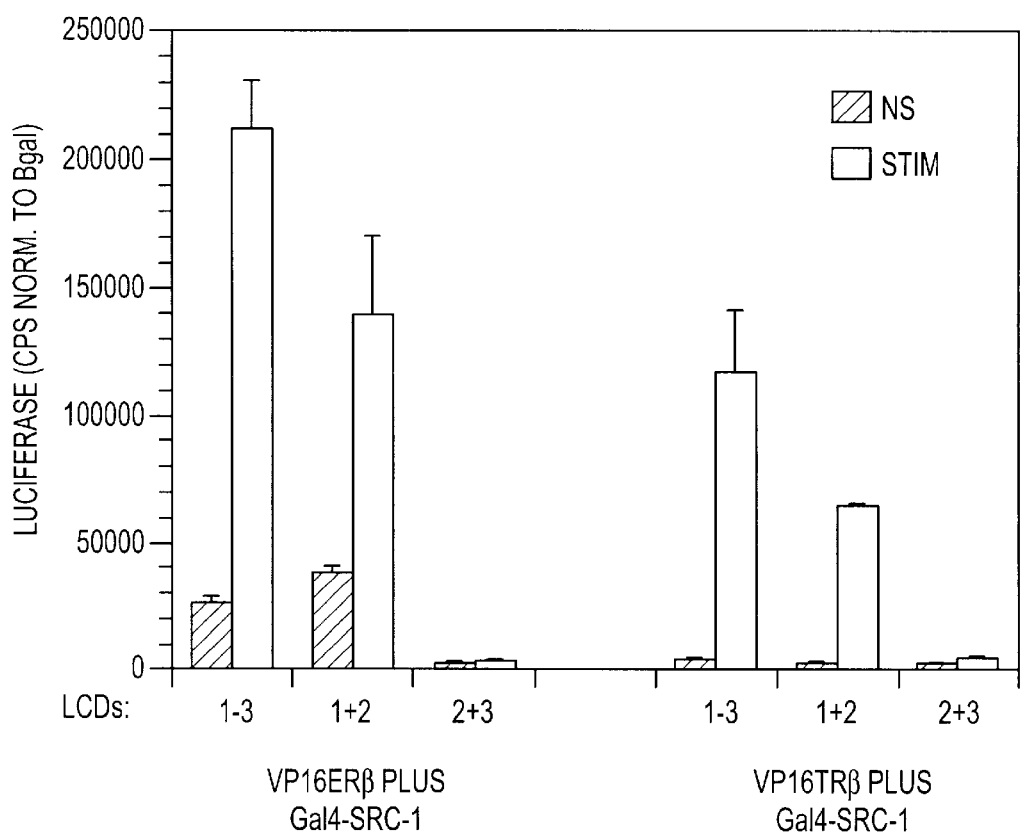
FIG. 11 shows that amino-terminal and carboxy-terminal truncations of SRC-1 fragment 597–781 (1–3) which remove LCD #1 (2+3) or #3 (1+2) were fused to Gal4 DBD. ERβ and TRβ do not require LCD #3 for hormone-inducible association, whereas LCD #1 is necessary. (ns=not stimulated; stim=stimulated with agonist ligand, estradiol for ER, T3 for TR).

FIG. 6 shows a schematic portrayal of LRB-TRX, CA-TRX, and CR-TRX constructs used and the reporter polynucleotide of a two-hybrid system. "Receptor" indicates LBD-TRX, with the LBD exemplified by a genereic nuclear receptor (NR) LBD with bound ligand (L), and the TRX domain represented by the VP16 acidic activation domain (VP16). "Coactivator" indicates a CA-TRX, with exemplary CA species being a portion of the SRC-1 protein, a portion of the CBP protein, or isolated LCD sequences from those proteins, the TRX domain is exemplified as the Gal4 DNA binding domain (DBD). "Corepressor" indicates a CR-TRX, with exemplary CR species being the interacting domains (ID1 or ID2) from SMRT or NcoR fused to the TRX domain as exemplified by Gal4 DNA binding domain (DBD). The reporter polynucleotide is exemplified as a UAS-TK-luciferase reporter containing binding sites for Gal4 DBD. CHO cells were triple transfected with these constructs and hormone added. FIG. 7 shows data from a positive two-hybrid system as a dose-response curve showing that reporter (luciferase) is generated only when all three components (VP16 ERα, Gal4-SRC-1, and UAS-TK-luciferase) are transfected together, and that the response is dose-dependent with respect to estradiol concentration. FIG. 8 shows data from a positive two-hybrid system as a dose-response curve showing that reporter (luciferase) is generated only when all three components (VP16 TRα, Gal4-SRC-1, and UAS-TK-luciferase) are transfected together, and that the response is dose-dependent with respect to T3 concentration. FIG. 9 shows ERα-Vp16 fusions tested against various LCDs in the absence (NS=no steroid present) or presence (E2=estradiol present) of agonistic ERα ligand. Numbers refer to amino acid position of N- and C-termini of fusion portion of coactivator using conventional numbering scheme. SRC 689–696 (LCD #2) appears specific for ERα. Note that these signals are approximately 10-fold lower than with SRC-1 containing 3 LCDs (compare to FIG. 7). FIG. 10 shows TRα-Vp16 fusions tested against various LCDs in the absence (NS=not stimulated) or presence (T3=triiodothyronine present) of agonistic TRα ligand. Numbers refer to amino acid position of N- and C-termini of fusion portion of coactivator using conventional numbering scheme. Note that these signals are approximately 10-fold lower than with SRC-1 containing 3 LCDs (compare to FIG. 8). FIG. 11 shows that amino-terminal and carboxy-terminal truncations of SRC-1 fragment 597–781 (1–3) which remove LCD #1 (2+3) or #3 (1+2) were fused to Gal4 DBD. ERβ and TRβ do not require LCD #3 for hormone-inducible association, whereas LCD #1 is necessary. (ns=not stimulated; stim=stimulated with agonist ligand, estradiol for ER, T3 for TR).

EXAMPLE 3

Positive Hybrid System:Corepressor

Figure 12:
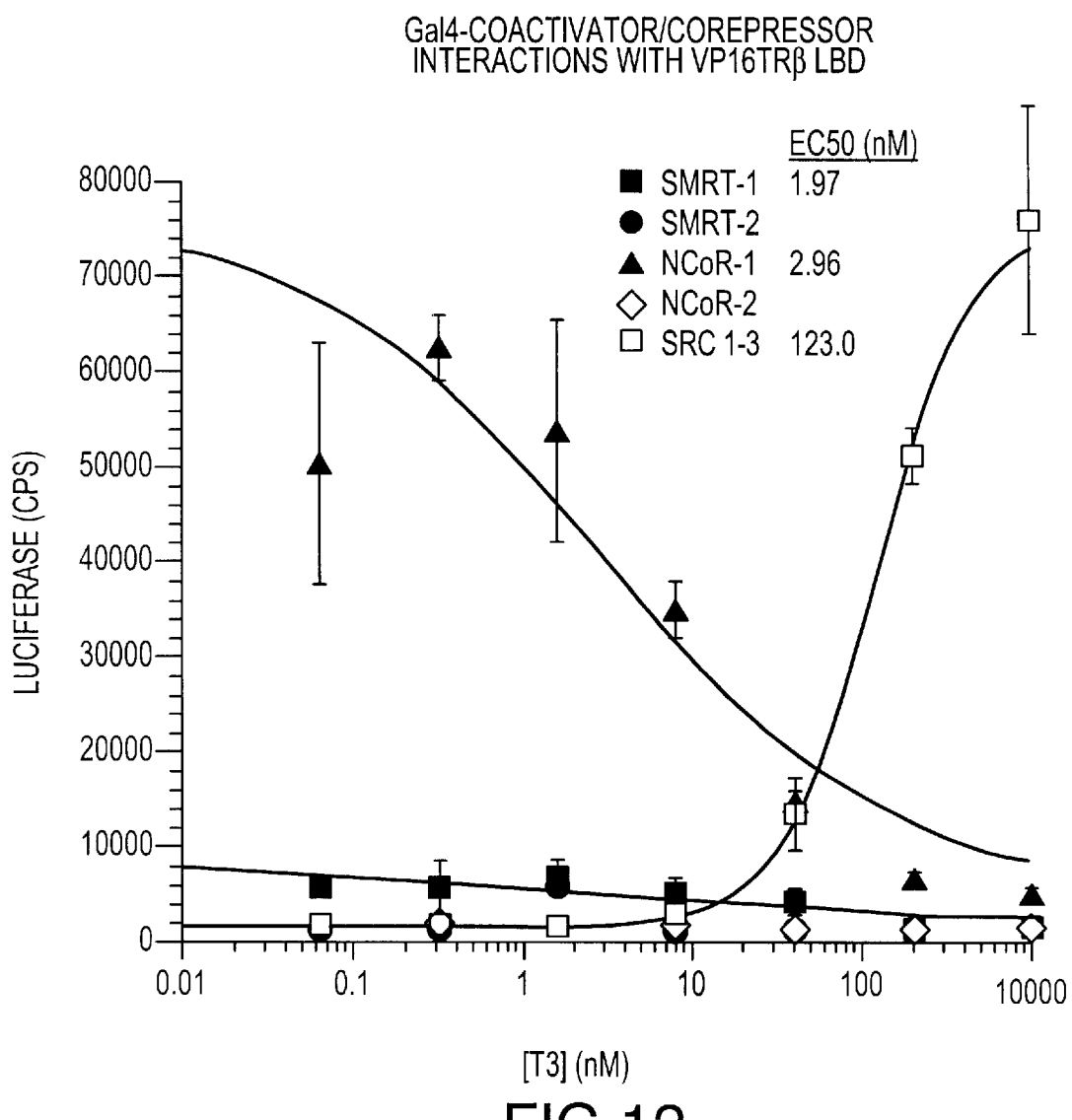
FIG. 12 shows coactivator/corepressor interactions with TRβ LBD in the positive two-hybrid system. NcoR ID1, and to a lesser extent SMRT ID1 interact with TRβ LBD, but neither ID2 interacts strongly with the LBD. T3 induced dissociation of the corepressor fragments at significantly lower concentrations than is required to recruit a coactivator.
Figure 13:
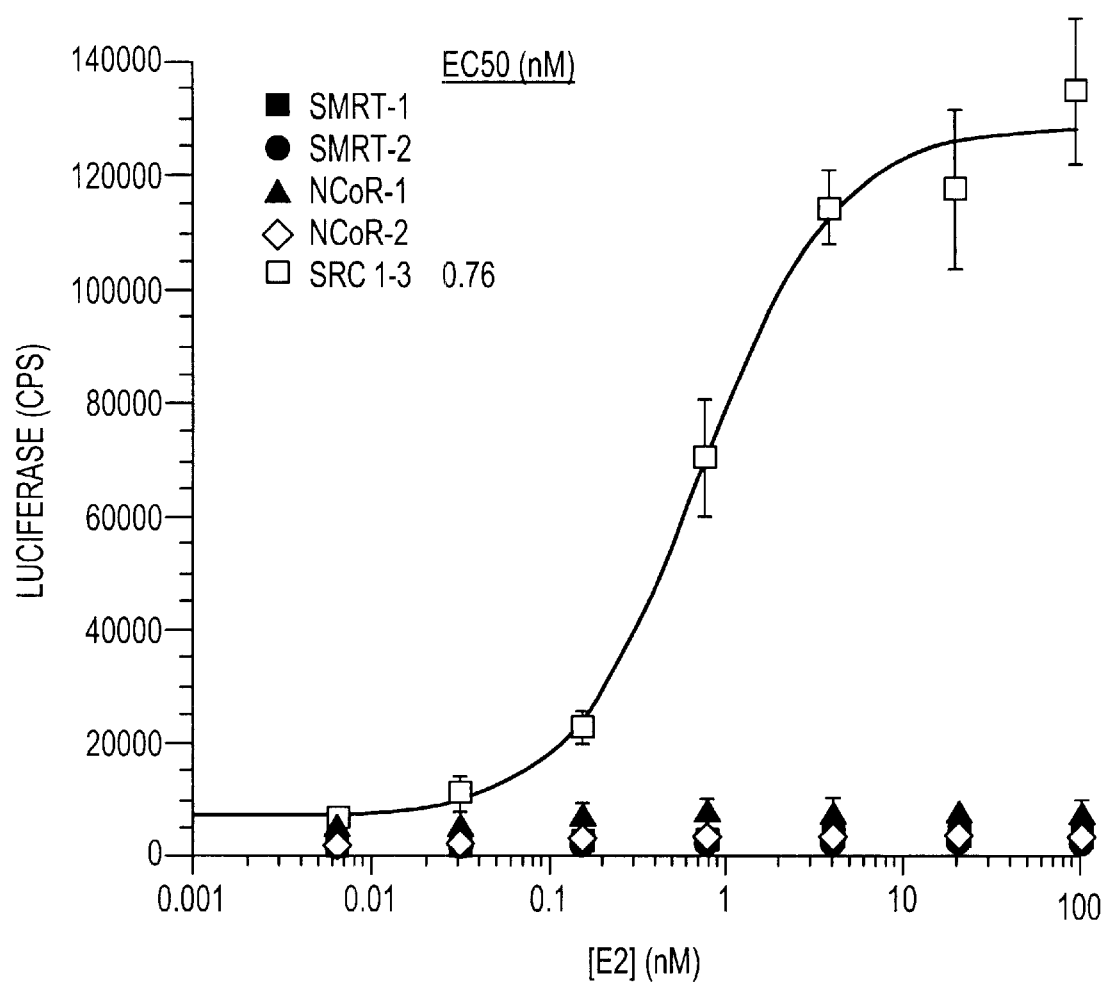
FIG. 13 shows coactivator/corepressor interactions with ERβ LBD in the positive two-hybrid system. NcoR ID1, and to a lesser extent SMRT ID1 interact with ERβ LBD, but neither ID2 interacts strongly with the LBD. None of the four Ids interact significantly with the ERβ LBD in the absence of ligand.

FIG. 12 shows coactivator/corepressor interactions with TRβ LED in the positive two-hybrid system. NcoR ID1, and to a lesser extent SMRT ID1 interact with TRβ LED, but neither ID2 interacts strongly with the LED. T3 induced dissociation of the corepressor fragments at significantly lower concentrations than is required to recruit a coactivator. FIG. 13 shows coactivator/corepressor interactions with ERβ LED in the positive two-hybrid system. NcoR ID1, and to a lesser extent SMRT ID1 interact with ERβ LBD, but neither ID2 interacts strongly with the LED. None of the four IDs interact significantly with the ERβ LED in the absence of ligand.

EXAMPLE 4

Identification of Novel LCDs

Figure 14:
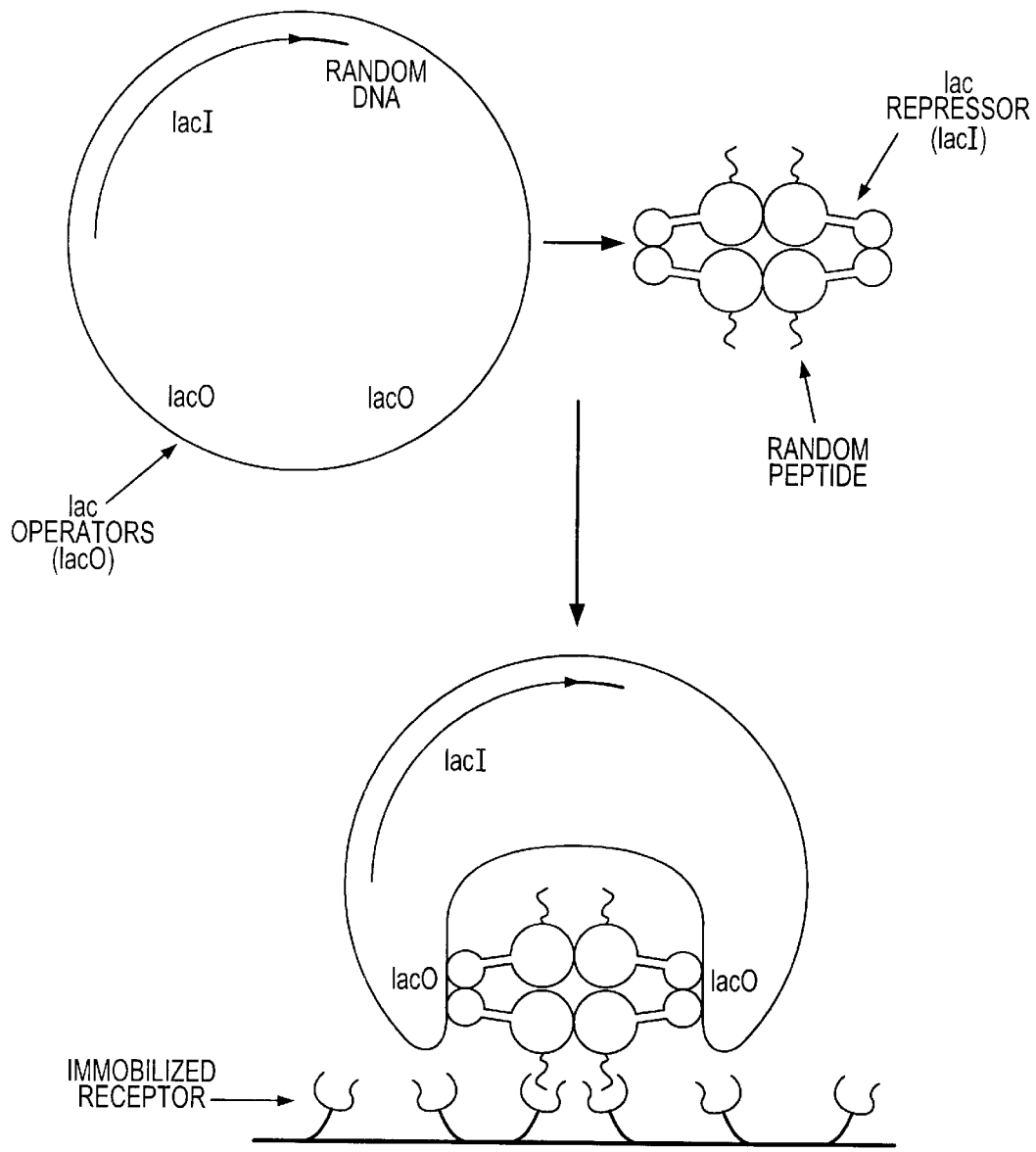
FIG. 14 shows a schematic portrayal of a method for identifying novel LCD sequences from libraries of displayed peptides. Peptide libraries were constructed by fusing sequences to the Lac repressor (LacI). The encoding plasmid contains operator sites so that a bacterial lysate contains the displayed peptides bound to the encoding plasmid. The library was screened with immobilized GST-ERβ in the presence of estradiol in four rounds of enrichment.
Figure 15:
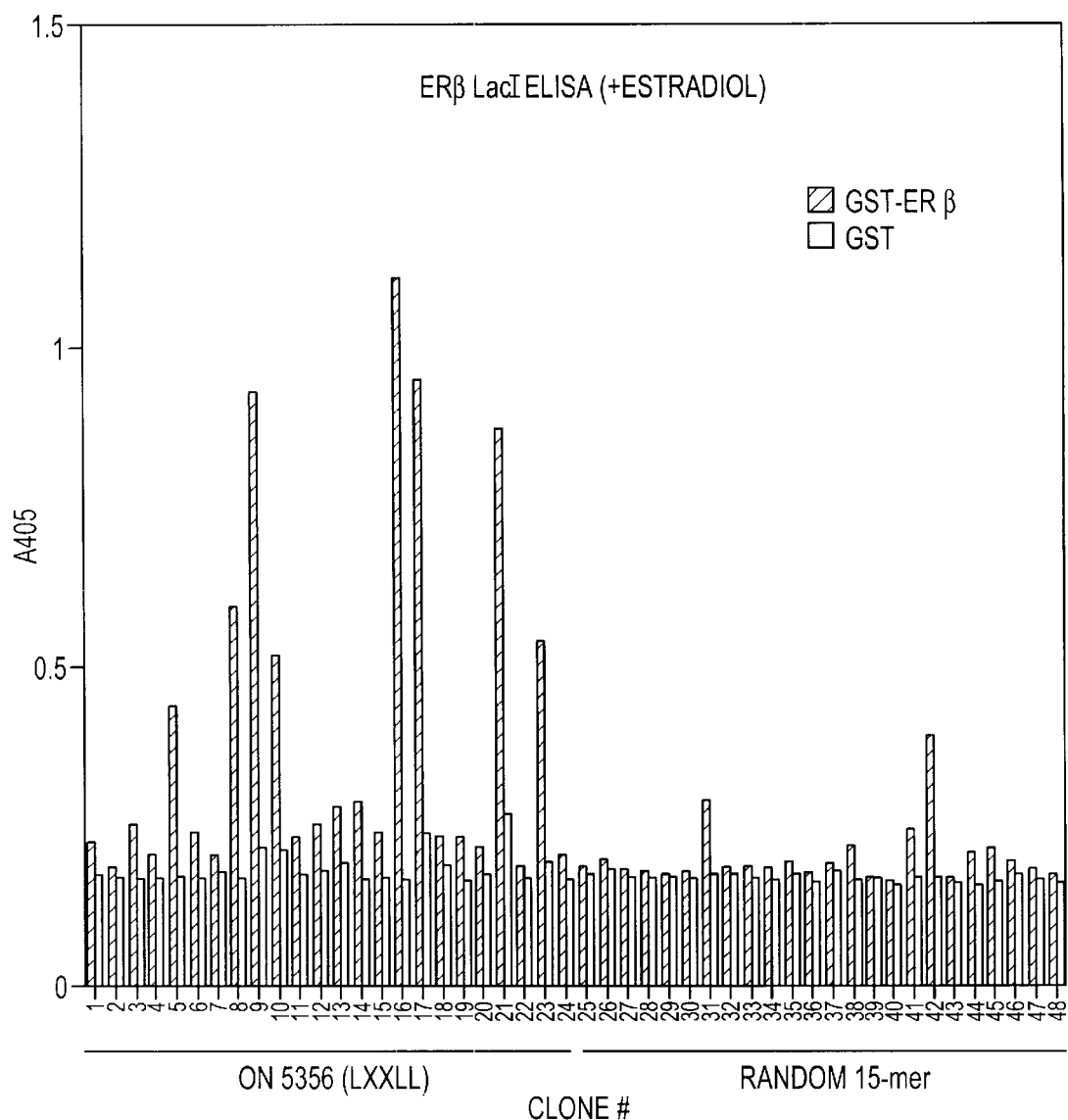
FIG. 15 shows ELISA signals for LacI-fused peptides obtained from either a focused (-LXXLL-) (SEQ ID NO:1) or random (-XXXXX-) (SEQ ID NO.2) 15 mer library in the presence of ERβ and estradiol.
Figure 17:
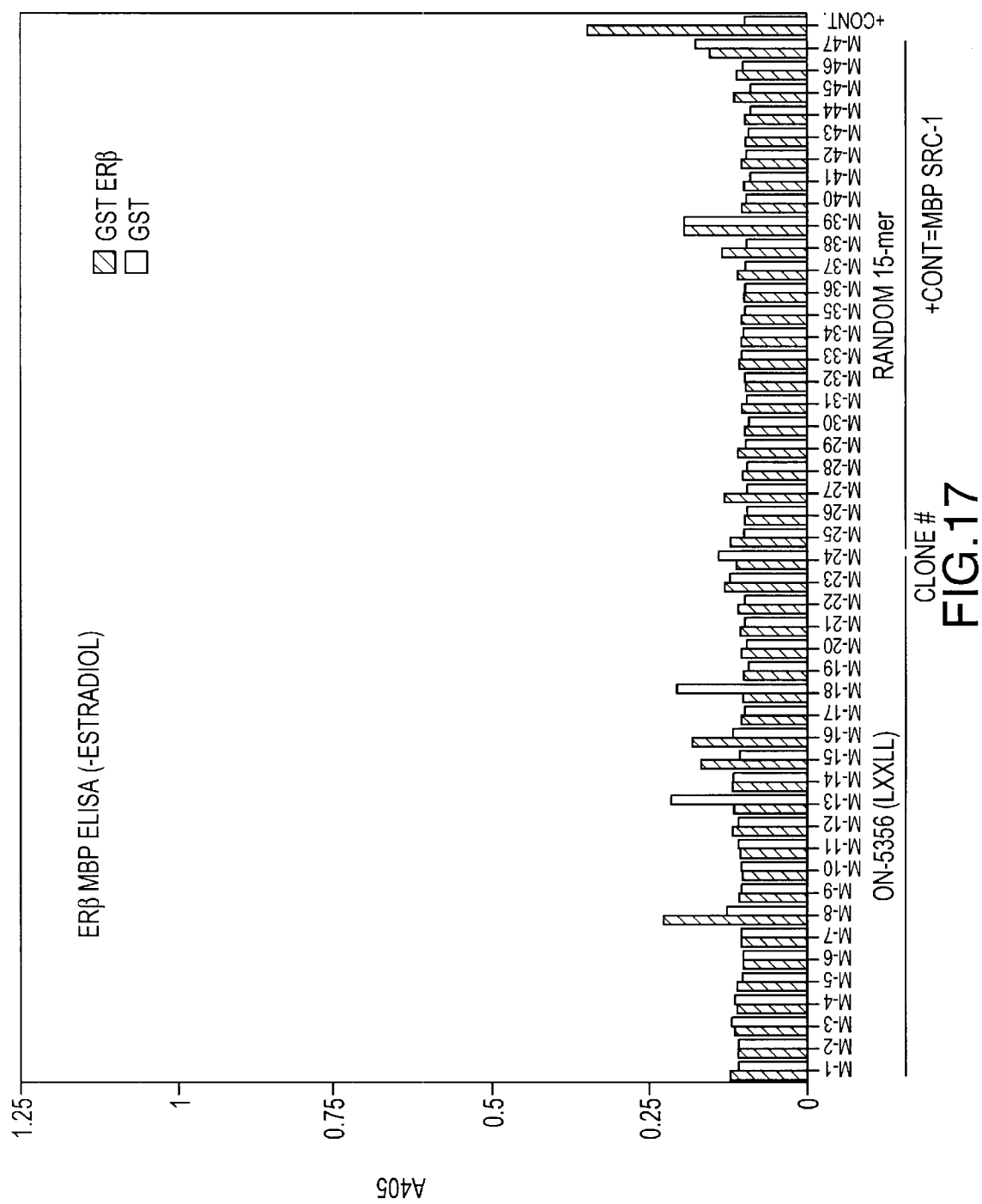
FIG. 17 shows ELISA data from the fourth round selectants of the LacI-fusions (tetravalent reagent) which were subcloned as a population into an MBP vector (monovalent reagent) and random clones tested without estradiol. Control is SRC-1 fragment (597–781) containing the 3 LCDs.
Figure 18:
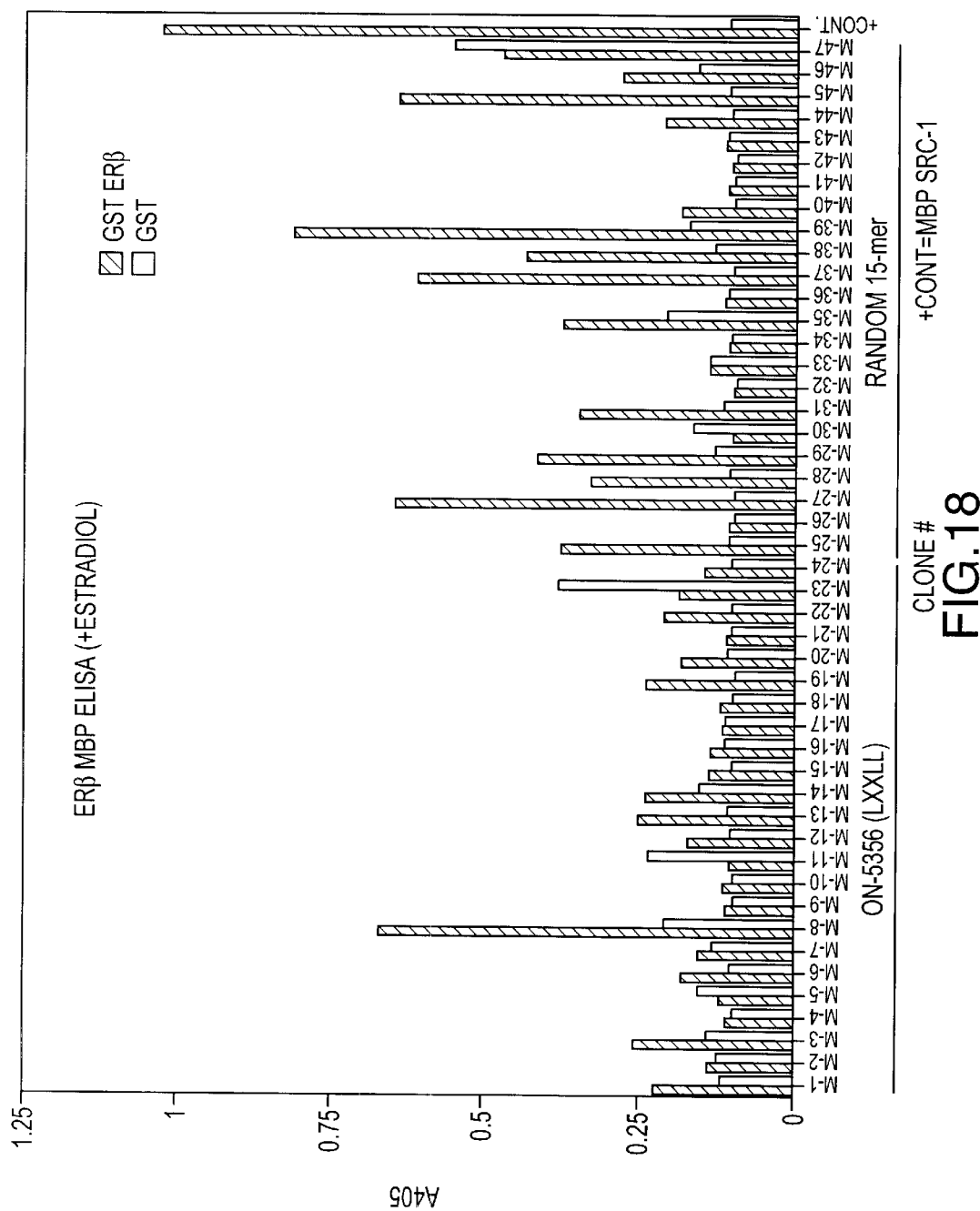
FIG. 18 shows ELISA data from the fourth round selectants of the LacI-fusions (tetravalent reagent) which were subcloned as a population into an MBP vector (monovalent reagent) and-random clones tested with estradiol. Control is SRC-1 fragment (597–781) containing the 3 LCDs. Note the estradiol dependence of many of the clones for interaction with ERβ (compare data in FIG. 17 with FIG. 18).

FIG. 14 shows a schematic portrayal of a method for identifying novel LCD sequences from libraries of displayed peptides. Peptide libraries were constructed by fusing sequences to the Lac repressor (LacI). The encoding plasmid contains operator sites so that a bacterial lysate contains the displayed peptides bound to the encoding plasmid. The library was screened with immobilized GST-ERβ in the presence of estradiol in four rounds of enrichment. FIG. 15 shows ELISA signals for LacI-fused peptides obtained from either a focused (-LXXLL-) (SEQ ID NO:1) or random (-XXXXX-) (SEQ ID NO.2) 15 mer library in the presence of ERβ and estradiol. FIG. 16 shows the sequences of LacI-fused peptides obtained by screening the library by ERβ panning. The top set of sequences (SEQ ID NOS:3 and 7–17) was obtained from the focused (-LXXLL-) (SEQ ID NO:1) library and the bottom set was (SEQ ID NOS:18–22) obtained from the random sequence (-XXXXX-) (SEQ ID NO:2) library. Notable amino acids are highlighted. FIG. 17 shows ELISA data from the fourth round selectants of the LacI-fusions (tetravalent reagent) which were subcloned as a population into an MBP vector (monovalent reagent) and random clones tested without estradiol. Control is SRC-1 fragment (597–781) containing the 3 LCDs. FIG. 18 shows ELISA data from the fourth round selectants of the LacI-fusions (tetravalent reagent) which were subcloned as a population into an MBP vector (monovalent reagent) and random clones tested with estradiol. Control is SRC-1 fragment (597–781) containing the 3 LCDs. Note the estradiol dependence of many of the clones for interaction with ERβ (compare data in FIG. 17 with FIG. 18). FIG. 19 shows the sequences (SEQ ID NOS:23–40) of the selected clones. Notable amino acid residues are highlighted.

The foregoing description of the preferred embodiments of the present invention has been presented for purposes of illustration and description. They are not intended to be exhaustive or to limit the invention to the precise form disclosed, and many modifications and variations are possible in light of the above teaching.

All publications and patent applications herein are incorporated by reference to the same extent as if each individual publication or patent application was specifically and individually indicated to be incorporated by reference.

Such modifications and variations which may be apparent to a person skilled in the art are intended to be within the scope of this invention.

---

SEQUENCE LISTING

```
<160> NUMBER OF SEQ ID NOS:  40

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:LBD (ligand
      binding domain) motif
<221> NAME/KEY: MOD_RES
<222> LOCATION: (2..3)
<223> OTHER INFORMATION: Xaa = any amino acid

<400> SEQUENCE: 1

Leu Xaa Xaa Leu Leu
  1               5

<210> SEQ ID NO 2
<211> LENGTH: 5
```

```
<212> TYPE: PRT
<213> ORGANISM: Artificial Sequence
<220> FEATURE:
<223> OTHER INFORMATION: Description of Artificial Sequence:random
      peptide
<221> NAME/KEY: MOD_RES
<222> LOCATION: (1..5)
<223> OTHER INFORMATION: Xaa = any amino acid

<400> SEQUENCE: 2

Xaa Xaa Xaa Xaa Xaa
  1               5

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:headpiece
      dimer derived peptide
<221> NAME/KEY: MOD_RES
<222> LOCATION: (1..19)
<223> OTHER INFORMATION: Xaa = any amino acid

<400> SEQUENCE: 3

Xaa Xaa Xaa Xaa Xaa Xaa Xaa Leu Xaa Xaa Leu Leu Xaa Xaa Xaa Xaa
  1               5                  10                  15

Xaa Xaa Xaa

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:LCD
      (leucine charged domain)

<400> SEQUENCE: 4

Lys Leu Val Gln Leu Leu Thr Thr Thr
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:LCD (leucine
      charged domain)

<400> SEQUENCE: 5

Ile Leu His Arg Leu Leu Gln Glu Gly
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:LCD (leucine
      charged domain)

<400> SEQUENCE: 6

Leu Leu Arg Tyr Leu Leu Asp Lys Asp
  1               5

<210> SEQ ID NO 7
<211> LENGTH: 15
<212> TYPE: PRT
```

```
<213> ORGANISM: Artificial Sequence
<220> FEATURE:
<223> OTHER INFORMATION: Description of Artificial Sequence:LacI-fused
      peptide from focused 15mer library

<400> SEQUENCE: 7

Val Leu Glu Lys Arg Pro Ile Leu Arg Glu Leu Leu Arg Gly Pro
  1               5                  10                  15

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 8

Gly Arg Asn Gly Ser Val Ile Leu Arg Arg Leu Leu Asn Ser Gly Gly
  1               5                  10                  15

Ser Tyr Ser Asn
            20

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 9

His Ser Met Asn His Ser Ile Leu Thr Arg Leu Leu Thr Ser Ser Val
  1               5                  10                  15

Gly Met Gln

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 10

Cys Ala Arg Asp Met Ser Lys Leu Gln Arg Leu Leu Arg Gly Leu Pro
  1               5                  10                  15

Ala

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 11

Val Gly Phe Ser Leu Arg Arg Leu Glu Thr Leu Leu Arg Glu Gly Arg
  1               5                  10                  15

Ile Asn Asp

<210> SEQ ID NO 12
<211> LENGTH: 15
<212> TYPE: PRT
```

```
<213> ORGANISM: Artificial Sequence
<220> FEATURE:
<223> OTHER INFORMATION: Description of Artificial Sequence:LacI-fused
      peptide from focused 15mer library

<400> SEQUENCE: 12

Thr Arg Arg Glu Ala Ser Lys Leu Cys Ser Leu Leu Ile Gly Gly
 1               5                  10                  15

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 13

Glu Thr Ala Lys Glu Ser Leu Leu Trp Arg Leu Leu Glu Arg Gly Ser
 1               5                  10                  15

Thr Glu Arg

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 14

Gln Leu Ala Ser Ser Ala Lys Leu Val Ser Leu Leu Gln Ser
 1               5                  10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 15

Arg Gly Asn Arg Leu Ser Arg Leu Ser Gln Leu Leu Gly Asn Ser Glu
 1               5                  10                  15

Ile Gly Gly

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence:LacI-fused
      peptide from focused 15mer library

<400> SEQUENCE: 16

Ser Ser His Lys Gly Ser Lys Leu Lys Ser Leu Leu Gln Phe Gly Pro
 1               5                  10                  15

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence:LacI-fused
      peptide from focused 15mer library
```

```
<400> SEQUENCE: 17

Gly Gly Ala Arg Asp Thr Met Leu Glu Ala Leu Leu Lys Cys Ser Gly
 1               5                  10                  15

Ala Gly Ile Asn
            20

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence:LacI-fused
      peptide from random 15mer library

<400> SEQUENCE: 18

Pro Ile Leu Arg Arg Leu Leu Thr Thr Arg Gln Met Arg Leu Ile
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:LacI-fused
      peptide from random 15mer library

<400> SEQUENCE: 19

Gly Pro Gln Thr Gly Ser Leu Leu Trp Lys Met Leu Ala Glu Arg
 1               5                  10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence:LacI-fused
      peptide from random 15mer library

<400> SEQUENCE: 20

Gly Ser Thr Met Ser Ile Leu Leu Ala Glu Arg Leu Leu Arg Arg Gly
 1               5                  10                  15

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence:LacI-fused
      peptide from random 15mer library

<400> SEQUENCE: 21

Ser Val Gly Ile Leu Arg Arg Leu Leu Glu Asn Lys Glu Glu
 1               5                  10

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence:LacI-fused
      peptide from random 15mer library

<400> SEQUENCE: 22

Arg Thr Gln Ser Leu Leu Arg Thr Leu Leu Thr Ala Asp Leu Thr
 1               5                  10                  15
```

```
<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence:Selected
      clone

<400> SEQUENCE: 23

Leu Cys Ser Thr Arg Pro Leu Leu Tyr Arg Leu Leu Leu Ser Lys Gly
 1               5                  10                  15

Cys Asn Trp

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:Selected
      clone

<400> SEQUENCE: 24

Lys Asp Ser Arg Ala His Leu Leu Arg Asp Val Leu Val Met Lys Ser
 1               5                  10                  15

Glu

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence:Selected
      clone

<400> SEQUENCE: 25

Gly Ser Lys His Gly Val Leu Leu Arg His Leu Leu Arg Arg Val Glu
 1               5                  10                  15

Glu Ser Arg

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence:Selected
      clone

<400> SEQUENCE: 26

Leu Arg Gly Arg Gln Pro Met Leu Arg Gly Leu Leu Cys Arg Ser Glu
 1               5                  10                  15

Val Arg Arg

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence:Selected
      clone

<400> SEQUENCE: 27

Glu Ser Cys His Arg Ser Leu Leu His Ser Leu Leu Leu Thr
 1               5                  10

<210> SEQ ID NO 28
```

```
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 28

Asp Thr Arg Met Thr Ile Leu Leu Arg Leu Leu Thr Asn Gln Ser
 1               5                  10                  15

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence:Selected
      clone

<400> SEQUENCE: 29

Gly Pro Gln Thr Ser Leu Leu Trp Lys Met Leu Ala Glu Arg
 1               5                  10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 30

Glu Cys Ser Ser Trp Leu Leu His Tyr Leu Arg Ser Arg Asp Ser
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence:Selected
      clone

<400> SEQUENCE: 31

Ser Ile Leu Leu Asn Leu Leu Thr Arg Lys Asp His Gln Trp Arg Asn
 1               5                  10                  15

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:Selected
      clone

<400> SEQUENCE: 32

Leu Leu Leu Lys Leu Leu Gln Arg Asn Pro
 1               5                  10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 33
```

```
Asn Leu Leu Met Arg Tyr Leu Met Ala Lys Ser Asp Gly Val Ser
  1               5                  10                 15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 34

Gly Arg Gly Leu Leu Glu Leu Leu Thr Arg Gly Asp Asn Ala
  1               5                  10                 15

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence:Selected
      clone

<400> SEQUENCE: 35

Gly Ser Leu Leu Glu Ser Leu Leu Arg Ser Arg Asp Gly
  1               5                  10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 36

Glu Arg Leu Pro Gly Arg Leu Leu Trp Arg Met Leu Met Glu Arg
  1               5                  10                 15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 37

Glu Ser Val Leu Leu Arg Leu Leu Arg Met Asp Ala Thr Arg Val
  1               5                  10                 15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 38

Trp Gly Ser Ser Leu Leu Val Thr Tyr Leu Thr Gln Arg Glu Met
  1               5                  10                 15

<210> SEQ ID NO 39
<211> LENGTH: 15
<212> TYPE: PRT
<213> ORGANISM: Artificial Sequence
<220> FEATURE:
```

-continued

```
<223> OTHER INFORMATION: Description of Artificial Sequence:Selected
      clone

<400> SEQUENCE: 39

Gln Met Gly Gly Pro Leu Leu Trp Ala Tyr Leu Ile Gly Pro Leu
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence:Selected
      clone

<400> SEQUENCE: 40

Gly Thr Gly Gly Ser Met Leu Leu Trp Tyr Leu Ser Lys Asp His
 1               5                  10                  15
```

What is claimed is:

1. A method for identifying nuclear receptor ligands comprising performing at least two different types of assays in multiplex format, said assays for identifying a ligand and/or quantifying the efficacy and/or potency of said ligand as an antagonist or agonist for a nuclear receptor and selected from the group of assays consisting of the following assay types (1) a positive hybrid system:coactivator assay, (2) a positive hybrid system:corepressor assay, (3) a reverse hybrid system:coactivator assay and (4) a reverse hybrid system:corepressor assay, wherein (a) the positive hybrid system:coactivator assay comprises (i) contacting a first fusion protein, a second fusion protein, a first test compound and a first reporter construct that comprises a first regulatory sequence responsive to a first transcription factor and a first reporter sequence operably linked thereto, and wherein the first fusion protein comprises a ligand binding domain (LBD) of the nuclear receptor linked to a transcriptional activation domain (AD) of the first transcription factor and the second fusion protein comprises a domain from a nuclear receptor coactivator protein (CA) and is linked to a DNA binding domain (DBD) of the first transcription factor, or the first and second fusion protein are as described in section (a)(i), except that the LBD of the first fusion protein is fused to the DBD of the first transcription factor and the CA domain of the second fusion protein is fused to the AD of the first transcription factor, whereby in the presence of agonist the first and second fusion proteins interact via the LBD and the CA domain to form a first reconstituted transcription factor that binds to the first regulatory sequence to activate transcription of the first reporter sequence; and (ii) determining whether expression of the first reporter sequence is activated, activation being an indication that the first test agent is a ligand for the nuclear receptor and is an agonist rather than an antagonist;

(b) the positive hybrid system:corepressor assay comprises (i) contacting a third fusion protein, a fourth fusion protein, a second test agent, and a second reporter construct that comprises a second regulatory sequence responsive to a second transcription factor and a second reporter sequence operably linked thereto, and wherein the third fusion protein comprises the LBD linked to an AD from a second transcription factor and the fourth fusion protein comprises a domain from a nuclear corepressor protein (CR) linked to a DBD of the second transcription factor, or the third and fourth fusion protein are as described in section (b) (i), except that the LBD of the third fusion protein is linked to the DBD of the second transcription factor and the CR domain of the fourth fusion protein is linked to the AD of the second transcription factor, whereby in the presence of antagonist the third and fourth fusion proteins interact via the LBD and the CR domain to form a second reconstituted transcription factor that binds to the second regulatory sequence to activate transcription of the second reporter sequence; and (ii) determining whether expression of the second reporter sequence is activated, activation being an indication that the second test agent is a ligand for the nuclear receptor and is an antagonist rather than an agonist;

(c) the reverse hybrid system:coactivator assay comprises (i) contacting a fifth fusion protein, a sixth fusion protein, a third test agent, a third reporter construct encoding a third reporter, and a first relay construct responsive to a third transcription factor and encoding a first relay product that inhibits expression of the third reporter; and wherein the fifth fusion protein comprises the LBD linked to an AD from the third transcription factor and the sixth fusion protein comprises the CA domain linked to the DBD of the third transcription factor, or the fifth and sixth fusion protein are as described in section (c)(i), except that the LBD of the fifth fusion protein is linked to the DBD of the third transcription factor and the CA domain of the sixth fusion protein is linked to the AD from the third transcription factor, whereby in the presence of antagonist, interaction between the fifth and sixth fusion protein via the LBD and the CA domain to form a third reconstituted transcription factor is inhibited, thereby inhibiting expression of the first relay product and thus activating expression of the third reporter; and (ii) determining whether expression of the third reporter is activated, activation being an indication that the third test agent is a ligand for the nuclear receptor and is an antagonist rather than an agonist; and (d) the reverse hybrid system:corepressor assay comprises (i) contacting a seventh fusion protein, an eight fusion protein, a fourth test agent, a fourth reporter construct encoding a fourth reporter, and a second relay construct responsive to a fourth transcription factor and encoding a second relay product that inhibits expression of the fourth reporter; and wherein the seventh fusion protein comprises the LBD linked to an AD from the fourth transcription factor and the eighth fusion protein comprises the CR domain linked to a DBD of the fourth transcription factor, or the seventh and eighth fusion protein are as described in section (d)(i), except that the LBD of the seventh fusion domain is linked to the DBD of the fourth transcription factor and the CR domain of the eighth fusion protein is linked to the AD from the fourth transcription factor, whereby in the presence of agonist, interaction between the seventh and eighth fusion protein via the LBD and the CR domain to form a fourth reconstituted transcription factor is inhibited, thereby inhibiting expression of the second relay product and activating expression of the fourth reporter; and (ii) determining whether expression of the fourth reporter is activated, activation being an indication that the fourth test agent is a ligand for the nuclear receptor and is an agonist rather than an antagonist.

2. The method of claim 1, wherein said at least two assays are selected from the group consisting of assay type (1), (3) and (4).

3. The method of claim 1, wherein said at least two assays are selected from the group of assays consisting of assay type (1), (2) and (4).

4. The method of claim 1, wherein said at least two assays are selected from the group of assays consisting of assay type (2), (3) and (4).

5. A method for identifying nuclear receptor ligands comprising performing at least two assays in multiplex format, said assays for identifying a ligand and/or quantifying the efficacy and/or potency of said ligand as an antagonist or agonist of a nuclear receptor and selected from the group of assays consisting of the following assay types (1) a positive hybrid system:coactivator assay, (2) a positive hybrid system:corepressor assay, (3) a reverse hybrid system:coactivator assay, (4) a reverse hybrid system:corepressor assay, (5) a direct interaction assay and (6) another assay for identifying and/or quantifying the efficacy and/or potency of nuclear receptor ligands, and wherein at least one of said assays is of assay type (2), (3) or (4) and assays (1), (2), (3) and (4) are performed as described in claim 1.

6. The method of claim 5, wherein at least one of said assays is of assay type (2) or (4).

7. A method for identifying nuclear receptor ligands comprising performing at least three assays in multiplex format, said assays for identifying a ligand and/or quantifying the efficacy and/or potency of said ligand as an antagonist or agonist of a nuclear receptor and selected from the group of assays consisting of the following assay types (1) a positive hybrid system:coactivator assay, (2) a positive hybrid system:corepressor assay, (3) a reverse hybrid system:coactivator assay, (4) a reverse hybrid system:corepressor assay and (5) a direct interaction assay, wherein of said at least three assays, at least three are of different assay types, and wherein assays (1), (2), (3) and (4) are performed as described in claim 1.

8. A method for identifying a candidate pharmaceutical agent from a library of test agents, wherein the candidate pharmaceutical agent has a desired biological effect profile and potentially affects binding between a nuclear receptor and a ligand, comprising:

performing at least three assays with each of a plurality of test agents from said library to obtain for each test agent measurements of a plurality of biological effects as detected as a ligand-induced conformational change or a binding interaction change as determined by said plurality of assays, said assays being selected from the group consisting of the following assay types (1) a positive hybrid system:coactivator assay, (2) a positive hybrid system:corepressor assay, (3) a reverse hybrid system:coactivator assay, (4) a reverse hybrid system:corepressor assay and (5) a direct interaction assay, wherein of said at least three assays, at least three are of different assay types;

assigning a separate score value for each of said biological effects based upon the detection or nondetection of a ligand-induced conformational change or binding interaction change in each of said plurality of assays to generate a score matrix for each of said test agents; and comparing said score matrix for each of said test agents to an equivalent score matrix for one or more predetermined agonist(s) and/or antagonist(s) to obtain an indication of the value of the test agent as a candidate pharmaceutical agent; and wherein (a) the positive hybrid system:coactivator assay comprises (i) contacting a first fusion protein, a second fusion protein, one of the test agents and a first reporter construct that comprises a first regulatory sequence responsive to a first transcription factor and a first reporter sequence operably linked thereto, and wherein the first fusion protein comprises a ligand binding domain (LBD) of the nuclear receptor linked to a transcriptional activation domain (AD) of the first transcription factor and the second fusion protein comprises a domain from a nuclear receptor coactivator protein (CA) and is linked to a DNA binding domain (DBD) of the first transcription factor, or the first and second fusion protein are as described in section (a)(i), except that the LBD of the first fusion protein is fused to the DBD of the first transcription factor and the CA domain of the second fusion protein is fused to the AD of the first transcription factor, whereby in the presence of agonist the first and second fusion proteins interact via the LBD and the CA domain to form a first reconstituted transcription factor that binds to the first regulatory sequence to activate transcription of the first reporter sequence; and (ii) determining whether expression of the first reporter sequence is activated, activation being an indication that the test agent is a ligand for the nuclear receptor and is an agonist rather than an antagonist;

(b) the positive hybrid system:corepressor assay comprises (i) contacting a third fusion protein, a fourth fusion protein, one of the test agents, and a second reporter construct that comprises a second regulatory sequence responsive to a second transcription factor and a second reporter sequence operably linked thereto, and wherein the third fusion protein comprises the LBD linked to an AD from a second transcription factor and the fourth fusion protein comprises a domain from a nuclear corepressor protein (CR) linked to a DBD of the second transcription factor, or the third and fourth fusion protein are as described in section (b)(i), except that the LBD of the third fusion protein is linked to the DBD of the second transcription factor and the CR domain of the fourth fusion protein is linked to the AD of the second transcription factor, whereby in the presence of antagonist the third and fourth fusion proteins interact via the LBD and the CR domain to form a second reconstituted transcription factor that binds to the second regulatory sequence to activate transcription of the second reporter sequence; and (ii) determining whether expression of the second reporter sequence is activated, activation being an indication that the test agent is a ligand for the nuclear receptor and is an antagonist rather than an agonist;

(c) the reverse hybrid system:coactivator assay comprises (i) contacting a fifth fusion protein, a sixth fusion protein, one of the test agents, a third reporter construct encoding a third reporter, and a first relay construct responsive to a third transcription factor and encoding a first relay product that inhibits expression of the third reporter; and wherein the fifth fusion protein comprises the LBD linked to an AD from the third transcription factor and the sixth fusion protein comprises the CA domain linked to the DBD of the third transcription factor, or the fifth and sixth fusion protein are as described in section (c)(i), except that the LBD of the fifth fusion protein is linked to the DBD of the third transcription factor and the CA domain of the sixth fusion protein is linked to the AD from the third transcription factor, whereby in the presence of antagonist, interaction between the fifth and sixth fusion protein via the LBD and the CA domain to form a third reconstituted transcription factor is inhibited, thereby inhibiting expression of the first relay product and thus activating expression of the third reporter; and (ii) determining whether expression of the third reporter is activated, activation being an indication that the test agent is a ligand for the nuclear receptor and is an antagonist rather than an agonist;

(d) the reverse hybrid system:corepressor assay comprises (i) contacting a seventh fusion protein, an eight fusion protein, one of the test agents, a fourth reporter construct encoding a fourth reporter, and a second relay construct responsive to a fourth transcription factor and encoding a second relay product that inhibits expression of the fourth reporter; and wherein the seventh fusion protein comprises the LBD linked to an AD from the fourth transcription factor and the eighth fusion protein comprises the CR domain linked to a DBD of the fourth transcription factor, or the seventh and eighth fusion protein are as described in section (d)(i), except that the LBD of the seventh fusion domain is linked to the DBD of the fourth transcription factor and the CR domain of the eighth fusion protein is linked to the AD from the fourth transcription factor, whereby in the presence of agonist, interaction between the seventh and eighth fusion protein via the LBD and the CR domain to form a fourth reconstituted transcription factor is inhibited, thereby inhibiting expression of the second relay product and activating expression of the fourth reporter; and (ii) determining whether expression of the fourth reporter is activated, activation being an indication that the test agent is a ligand for the nuclear receptor and is an agonist rather than an antagonist; and (e) the direct interaction assay comprises (i) contacting a ligand binding domain from a nuclear receptor and a coactivation domain or corepressor domain in the presence of one of the test agents; and (ii) detecting binding between the nuclear receptor and the coactivation or corepressor domains.

9. The method of claim 8, wherein said plurality of assays are greater than 2 and less than 10 billion in number.

10. The method of claim 9, wherein said plurality of assays are at least 5 in number.

11. The method of claim 8, wherein said score value is a binary value.

12. The method of claim 8, wherein said score value is a quantitative value.

13. The method of claim 8, wherein said test agent is a mixture of test agents.

14. The method of claim 8, wherein the score matrix and the equivalent score matrix are compared by rank ordering of matrix similarity.

15. The method of claim 8, wherein the score matrix and the equivalent score matrix are compared by electronic computation using a trained neural network implementation.

16. A method for identifying a candidate pharmaceutical agent from a library of test agents, wherein the candidate pharmaceutical agent has a desired biological effect profile and potentially affects binding between a nuclear receptor and a ligand, comprising:

(a) performing a plurality of assays with each of a plurality of test agents from said library to obtain for each test agent measurements of a plurality of biological effects as detected as a ligand-induced conformational change or a binding interaction change as determined by said plurality of assays, said plurality of assays being selected from the group consisting of the following assay types (1) a positive hybrid system:coactivator assay, (2) a positive hybrid system:corepressor assay, (3) a reverse hybrid system:coactivator assay, and (4) a reverse hybrid system:corepressor assay, wherein at least two of the plurality of assays are of different assay types;

(b) assigning a separate score value for each of said biological effects based upon the detection or nondetection of a ligand-induced conformational change or binding interaction change in each of said plurality of assays to generate a score matrix for each of said test agents; and (c) comparing said score matrix for each of said test agents to an equivalent score matrix for one or more predetermined agonist(s) and/or antagonist(s) to obtain an indication of the value of the test agent as a candidate pharmaceutical agent; and wherein assays (1), (2), (3) and (4) are performed as described in claim 8.

17. A method for identifying a candidate pharmaceutical agent from a library of test agents, wherein the candidate pharmaceutical agent has a desired biological effect profile and potentially affects binding between a nuclear receptor and a ligand, comprising:

(a) performing a plurality of assays with each of a plurality of test agents from said library to obtain for each test agent measurements of a plurality of biological effects as detected as a ligand-induced conformational change or a binding interaction change as determined by said plurality of assays, said plurality of assays being selected from the group consisting of the following assay types (1) a positive hybrid system:coactivator assay, (2) a positive hybrid system:corepressor assay, (3) a reverse hybrid system:coactivator assay, (4) a reverse hybrid system:corepressor assay, (5) a direct interaction assay and (6) another assay for identifying and/or quantifying the efficacy and/or potency of nuclear receptor ligands, and wherein at least one of said assays is of assay type (2), (3) or (4);

(b) assigning a separate score value for each of said biological effects based upon the detection or nondetection of a ligand-induced conformational change or binding interaction change in each of said plurality of assays to generate a score matrix for each of said test agents; and (c) comparing said score matrix for each of said test agents to an equivalent score matrix for one or more predetermined agonist(s) and/or antagonist(s) to obtain an indication of the value of the test agent as a candidate pharmaceutical agent; and wherein assays (1), (2), (3), (4) and (5) are performed as described in claim 8.

* * * * *